US008222469B2

(12) United States Patent
Schrock et al.

(10) Patent No.: US 8,222,469 B2
(45) Date of Patent: *Jul. 17, 2012

(54) CATALYSTS AND PROCESSES FOR THE FORMATION OF TERMINAL OLEFINS BY ETHENOLYSIS

(75) Inventors: Richard R. Schrock, Winchester, MA (US); Smaranda C. Marinescu, Cambridge, MA (US); Amir H. Hoveyda, Lincoln, MA (US)

(73) Assignees: Massachusetts Institute of Technology, Cambridge, MA (US); Trustees of Boston College, Chestnut Hill, MA (US)

( * ) Notice: Subject to any disclaimer, the term of this patent is extended or adjusted under 35 U.S.C. 154(b) by 157 days.

This patent is subject to a terminal disclaimer.

(21) Appl. No.: 12/503,608

(22) Filed: Jul. 15, 2009

(65) Prior Publication Data
US 2011/0015430 A1  Jan. 20, 2011

(51) Int. Cl.
*C07C 2/02* (2006.01)
(52) U.S. Cl. ........ 585/502; 560/205; 585/500; 502/155; 502/162; 502/167
(58) Field of Classification Search .................... None
See application file for complete search history.

(56) References Cited

U.S. PATENT DOCUMENTS

| | | |
|---|---|---|
| 5,055,628 A | 10/1991 | Lin et al. |
| 5,889,128 A | 3/1999 | Schrock et al. |
| 6,121,473 A | 9/2000 | Schrock et al. |
| 6,271,325 B1 | 8/2001 | McConville et al. |
| 6,306,988 B1 | 10/2001 | Grubbs et al. |
| 6,316,555 B1 | 11/2001 | Schrock et al. |
| 6,346,652 B1 | 2/2002 | Schrock et al. |
| 6,414,097 B1 | 7/2002 | Grubbs et al. |
| 6,610,806 B2 | 8/2003 | Schrock et al. |
| 6,677,495 B1 | 1/2004 | Schwab et al. |
| 6,855,839 B2 | 2/2005 | McConville et al. |
| 7,135,544 B2 | 11/2006 | Schrock et al. |
| 7,932,397 B2 | 4/2011 | Hock et al. |
| 2008/0119678 A1 | 5/2008 | Hock et al. |
| 2010/0305354 A1 | 12/2010 | Dubois et al. |
| 2011/0065915 A1 | 3/2011 | Malcolmson et al. |
| 2011/0077421 A1 | 3/2011 | Schrock et al. |

FOREIGN PATENT DOCUMENTS

| | | |
|---|---|---|
| DE | 19654166 A1 | 6/1998 |
| EP | 1693357 A1 | 8/2006 |
| WO | WO 96/04289 A1 | 2/1996 |
| WO | WO 2008/155506 A1 | 12/2008 |

OTHER PUBLICATIONS

Flook et al (J.Am.Chem.Soc. 2009, 131, 7962-7963).*
Attygalle et al., Azamacrolides: a family of alkaloids from the pupal defensive secretion of a ladybird beetle (*Epilachna varivestis*). Proc Natl Acad Sci U S A. Jun. 1, 1993;90(11):5204-8.
Barluenga et al. Zirconium-mediated coupling reactions of amines and enol or allyl ethers: synthesis of allyl- and homoallylamines. Chemistry. Jan. 5, 2004;10(1):109-16.
Bindl et al., Molybdenum nitride complexes with Ph3SiO ligands are exceedingly practical and tolerant precatalysts for alkyne metathesis and efficient nitrogen transfer agents. J Am Chem Soc. Jul. 15, 2009;131(27):9468-70.
Bollag et al., Epothilones, a new class of microtubule-stabilizing agents with a taxol-like mechanism of action. Cancer Res. Jun. 1, 1995;55(11):2325-33.
Coutelier et al., Terminal alkyne metathesis: a further step towards selectivity. Adv Synth Catal. 2006;348:2038-42.
Deiters et al., Synthesis of oxygen- and nitrogen-containing heterocycles by ring-closing metathesis. Chem Rev. May 2004;104(5):2199-238.
Fox et al., Synthesis of five- and six-coordinate alkylidene complexes of the type Mo(CHR)(NAr)[OCMe(CF3)2]2Sx and their use as living Romp initiators or Wittig reagents. Organometallics. 1993;12(3):759-68.
Freudenberger et al., Multiple metal-carbon bonds. 37. Preparation of di-tert-butoxytungsten(VI) alkylidene complexes by protonation of tri-tert-butoxytungsten(VI) alkylidyne complexes. Organometallics. 1985;4(11):1937-44.
Fürstner et al., Macrocycles by ring-closing metathesis. Synthesis. 19973:792-803.
Fürstner et al., Total synthesis of the turrianes and evaluation of their DNA-cleaving properties. Chem Eur J. 2002;8:1856-71.
Garber et al., Efficient and recyclable monomeric and dendritic Ru-based metathesis catalysts. J Am Chem Soc. 2000;122(34):8168-79.
Gradillas et al., Macrocyclization by ring-closing metathesis in the total synthesis of natural products: reaction conditions and limitations. Angew Chem Int Ed Engl. Sep. 18, 2006;45(37):6086-101.
Heppekausen et al. Practical new silyloxy-based alkyne metathesis catalysts with optimized activity and selectivity profiles. J Am Chem Soc. Aug. 18, 2010;132(32):11045-57.
Herrmann et al. Methyltrioxorhenium als katalysator für die Olefin-Metathese. Angewandte Chemie. 1991;103(12):1704-6. German.
Hofle et al., Epothilone A and B—novel 16-membered macrolides with cytotoxic activity: Isolation, crystal structure, and conformation in solution. Angew Chem. Int Edn. 1996;35:1567-9.
Hoveyda et al., The remarkable metal-catalysed olefin metathesis reaction. Nature. Nov. 8, 2007;450(7167):243-51.
International Search Report and Written Opinion in connection with PCT/US2010/002644, mailed Mar. 7, 2011.
Kobayashi et al., Nakadomarin A, a Novel Hexacyclic Manzamine-Related Alkaloid from Amphimedon Sponge. J Org Chem. 1997;62(6):9236-9.
Kowalski et al., Activities of the microtubule-stabilizing agents epothilones A and B with purified tubulin and in cells resistant to paclitaxel (Taxol(R)). J Biol Chem. Jan. 24, 1997;272(4):2534-41.
Meng et al., Total syntheses of epothilones A and B. J Am Chem Soc. 1997;119;42:10073-92.

(Continued)

*Primary Examiner* — Sudhakar Katakam
(74) *Attorney, Agent, or Firm* — Andrea L. C. Robidoux; Choate Hall & Stewart LLP

(57) ABSTRACT

The present invention relates generally to catalysts and processes for the formation of terminal olefin(s) from internal olefin(s) via ethenolysis reactions. The ethenolysis reactions may proceed with high conversion, high turnover, and/or high selectivity.

36 Claims, 3 Drawing Sheets

OTHER PUBLICATIONS

Nagata et al., The first total synthesis of nakadomarin A. J Am Chem Soc. 2003;125:7484-5.

Nicolaou et al., Metathesis reactions in total synthesis. Angew Chem Int Ed Engl. Jul. 18, 2005;44(29):4490-527.

Nicolaou et al., Synthesis of epothilones A and B in solid and solution phase. Nature. May 15, 1997;387(6630):268-72. Erratum in: Nature Nov. 6, 1997;390(6655):100.

Nicolaou et al., The olefin metathesis approach to epothilone A and its analogues. J Am Chem Soc. 1997;119(34):7960-73.

Nilson et al., Total synthesis of (−)-nakadomarin A. Org Lett. Nov. 5, 2010;12(21):4912-5.

Ono et al., Asymmetric total synthesis of (−)-nakadomarin A. Angew Chem Int Ed Engl. Apr. 2, 2004;43(15):2020-3.

Quintard et al., Synthesis and Conformational Analysis of Macrocycles Related to 10-Oxa-epothilone. Eur J Org Chem. Nov. 15, 2004;2004(23):4762-70.

Rossini et al., Antiinsectan activity of epilachnene, a defensive alkaloid from pupae of Mexican bean beetles (*Epilachna varivestis*). J Chem Ecol. 2000;26:391-7.

Schinzer et al., Total Synthesis of (−)-Epothilone A. Chem Eur J. 1999;5:2483-91.

Scholl et al., Synthesis and activity of a new generation of ruthenium-based olefin metathesis catalysts coordinated with 1,3-dimesityl-4,5-dihydroimidazol-2-ylidene ligands. Org Lett. Sep. 23, 1999;1(6):953-6.

Schrock et al., High-oxidation-state molybdenum and tungsten alkylidyne complexes. Acc Chem Res. 1986;19(11):342-8.

Schrock et al., Molybdenum and tungsten imido alkylidene complexes as efficient olefin-metathesis catalysts. Angew Chem Int Ed Engl. Oct. 6, 2003;42(38):4592-633.

She et al., Examination of the olefin—olefin ring-closing metathesis to prepare latrunculin B. Tetrahedron Lett. 2009;50:298-301.

Smith et al., Total synthesis of (±)-haliclonacyclamine C. Angew Chem Int Edn. 2010;49:1599-1602.

Wang et al., Control of olefin geometry in macrocyclic ring-closing metathesis using a removable silyl group. J Am Chem Soc. 2011;133(24):9196-9.

Xu et al., Applications of Zr-Catalyzed Carbomagnesation and Mo-Catalyzed Macrocyclic Ring Closing Metathesis in Asymmetric Synthesis. Enantioselective Total Synthesis of Sch 38516 (Fluvirucin B1). J Am Chem Soc. 1997;119(43):10302-16.

Young et al., Total synthesis of (+)-Nakadomarin A. J Am Chem Soc. 2007;129(5):1465-9.

Zhao et al. Endo-selective enyne ring-closing metathesis promoted by stereogenic-at-W mono-pyrrolide complexes. Org Lett. Feb. 18, 2011;13(4):784-7.

[No Author Listed] New catalysts promise faster, cleaner, and more efficient research platform. Science Daily. Nov. 16, 2008. 2 pages.

Aeilts et al., A readily available and user-friendly chrial catalyst for efficient enantioselective olefin metathesis. Angew Chem Int Ed. 2001;40(8):1452-6.

Agbossou et al., Synthesis and Reactivity of Chiral Rhenium Alcohol Complexes of the Formula [($\eta^5$C$_5$H$_5$)Re(NO)(PPh$_3$)(ROH)]$\oplus$ BF$_4\ominus$. Chem Berichte. 1990;123(6):1293-9.

Al Obaidi et al., Steric and electronic effects on the chemistry of molybdenum octahedrally co-ordinated by six nitrogen atoms. The molecular structure of [Mo{HB(3,5-Me$_2$C$_3$ N$_2$H$_3$)} (NO)(pyrollide)$_2$]. J Chem Soc Chem Commun. 1984;(11): 690-2.

Anderson et al., Kinetic selectivity of olefin metathesis catalysts bearing cyclic (alkyl)(amino)carbenes. Organometallics. 2008;27(4):563-6.

Ascenso et al., Synthesis and characterization of [W(NC$_4$Me$_4$)$_2$Cl$_2$] and [W(NC$_4$Me$_4$)$_2$(CH$_3$)$_2$], the first azametallocene tungsten complexes with pyrrolyl ligands. Electronic structure and bonding of tungsten bispyrrolyl complexes. Inorg Chem Acta. 2003; 356: 249-58.

Bailey et al., Evaluation of molybdenum and tungsten metathesis catalysts for homogeneous tandem alkane metathesis:organometallics. 2009;28(1):355-60.

Bazan et al., Living ring-opening metathesis polymerization of 2,3-difunctionalized 7-oxanorbornenes and 7-oxanorbornadienes by Mo(CHCMe2R)(NC6H3-iso-Pr2-2,6)(O-tert-Bu)2 and Mo(CH CMe2R)(NC6H3-iso-Pr2-2,6)(OCMe2CF3)2. J Am Chem Soc. 1991;113(18):6899-907.

Bei et al., Highly efficient olefin-metathesis catalysts. Pharm Technol. 2008:s18.

Blackwell et al., Enediynes via sequential acetylide reductive coupling and alkyne metathesis: Easy access to well-defined molybdenum initiators for alkyne metathesis. Organometallics. 2003;22: 3351-53.

Blackwell et al., New approaches to olefin cross-metathesis. J Am Chem Soc. 2000;122:58-71.

Blanc et al., Dramatic improvements of well-defined silica supported mo-based olefin metathesis catalysts by tuning the n-containing ligands. J Am Chem Soc. 2007;129(27):8434-5.

Blanc et al., Highly active, stable, and selective well-defined silica supported mo imido olefin metathesis catalysts. J Am Chem Soc. 2007; 129(17):1044-1045.

Blanc et al., Surface versus molecular siloxy ligands in well-defined olefin metathesis catalysis: [{(RO)$_3$SiO} Mo(=NAr) (= CH$t$Bu)(CH$_2$$t$Bu)]. Angew Chem Int Ed. 2006;45:1216-20.

Bornand et al., Mechanism-based design of a ROMP catalyst for sequence-selective copolymerization. Angew Chem Int Ed Engl. Dec. 9, 2005;44(48):7909-11.

Brunner et al., Catalytic hydrosilylation or hydrogenation at one coordination site of [Cp'Fe(CO)(X)] fragments. Angewandte Chemie Intl Ed Engl. Oct 1990;29(10):1131-2.

Brunner et al., Optisch aktive Übergangsmetall-Komplexe, LI: P-Liganden als optisch aktive Hilfsstoffe in den Komplexen C5H5M(CO)(NO)L, M = Cr, Mo, W. Chem Ber. 1978;111:673-91.

Brunner, Optical activity at an asymmetrical manganese atom. Angew Chem, Int Ed Engl. 1969;8:382-3.

Brunner, Optically active organometallic compounds of transition elements with chiral metal atoms. Angew Chemie Intl Ed. May 3, 1999;38(9):1194-1208.

Brunner, Stability of the metal configuration in chiral-at-metal half-sandwich compounds. Eur J Inorg Chem. 2001:905-12.

Burdett et al., Renewable monomer feedstocks via olefin metathesis: fundamental mechanistic studies of methyl oleate ethenolysis with the first-generation grubbs catalyst. Organometallics. 2004;23(9):2027-47.

Cantrell et al., Ring-opening Metathesis of a cyclic imine. Organometallics. Aug. 2, 2000;19(18):3562-68.

Chatterjee et al., Olefin Cross-Metathesis. Handbook Metathesis. 2003;2:246-95.

Connon et al., Recent developments in olefin cross-metathesis. Angew Chem Int Ed Engl. Apr. 29, 2003;42(17):1900-23.

Corma et al., Chemical routes for the transformation of biomass into chemicals. Chem Rev. Jun. 2007;107(6):2411-502. Epub May 30, 2007.

Dias et al., Synthesis, characterisation, crystal structure, reactivity and bonding in titanium complexes containing 2,3,4,5-tetramethylpyrrolyl. J Chem Soc, Dalton Trans. 1997;1055-61.

Dinger et al., High turnover numbers with ruthenium-based metathesis catalysts. Adv Synth Catal. Aug 2002;344(6-7):671-7.

Dolman et al., Efficient catalytic enantioselective synthesis of unsaturated amines: preparation of small- and medium-ring cyclic amines through mo-catalyzed asymmetric ring-closing metathesis in the absence of solvent. J Am Chem Soc. Jun. 19, 2002;124(24):6991-7.

Dolman, New chiral molybdenum metathesis catalysts; application of the enantioselective preparation of cyclic amines. Ph.D. Thesis. MIT. Jun. 2004. 234 pages.

Duarte et al., Chlorobis(dimethylamido)($\eta^5$-2,5-dimethylpyrroly)titanium(IV), [Ti(NMe$_2$)$_2$(DMP)Cl]. Acta Cryst. 2005;C61:m104-6.

Feldman et al., Recent advances in the chemistry of "d$^0$" alkylidine metallacyclobutane complexes. Prog Inorg Chem. 1991;39:1-74.

Flook et al., Z-selective olefin metathesis processes catalyzed by a molybdenum hexaisopropylterphenoxide monopyrrolide complex. J Am Chem Soc. Jun. 17, 2009;131(23):7962-3.

Fontecave et al., Chiral-at-metal complexes as asymmetric catalysts. In Chiral Diazaligands for Asymmetric Synthesis. Top Organometallic Chem. 2005;15(2005):271-88.

Forman et al., A stable ruthenium catalyst for productive olefin metathesis. Organometallics. 2004;23(21):4824-7.

Fürstner et al., Alkyne metathesis: Development of a novel molybdenum-based catalyst system and its application to the total synthesis of epothilone A and C. Chem Eur J. 2001;7(24):5299-5317.

Fürstner et al., Mo[N($t$-Bu)(Ar)]$_3$ complexes as catalyst precursors: in situ activation and application to metathesis reactions of alkynes and diynes. J Am Chem Soc. 1999;121(40):9453-54.

Furstner et al., Cationic ruthenium allenylidene complexes as catalysts for ring closing olefin metathesis. Chemistry. May 15, 2000;6(10):1847-57.

Ganter, Chiral organometallic half-sandwich complexes with defined metal configuration. Chem Soc Rev. May 2003;32(3):130-8.

Giessert et al., Intermolecular enol ether-alkyne metathesis. Org Lett. May 15, 2003;5(10):1793-6.

Gillingham et al., Chiral N-heterocyclic carbenes in natural product synthesis: application of Ru-catalyzed asymmetric ring-opening/cross-metathesis and Cu-catalyzed allylic alkylation to total synthesis of baconipyrone C. Angew Chem Int Ed Engl. 2007;46(21):3860-4.

Giudici et al., Directed catalytic asymmetric olefin metathesis. Selectivity control by enoate and ynoate groups in Ru-catalyzed asymmetric ring-opening/cross-metathesis. J Am Chem Soc. Apr. 4, 2007;129(13):3824-5. Epub Mar. 8, 2007.

Hadlington et al., Catalyst flexes for extra control. Chemistry World. Nov. 17, 2008. Last accessed online. Dec. 1, 2008.

Hesek et al., The first asymmetric synthesis of chiral ruthenium tris(bipyridine) from racemic ruthenium bis(bipyridine) complexes. Tetrahedron Lett. Apr. 8, 2000;41(15):2617-20.

Hock et al., Dipyrrolyl precursors to bisalkoxide molybdenum olefin metathesis catalysts. J Am Chem Soc. 2006:128(50):16373-5.

Ibrahem et al., Highly Z- and enantioselective ring-opening/cross-metathesis reactions catalyzed by stereogenic-at-Mo adamantylimido complexes. J Am Chem Soc. Mar. 25, 2009;131(11):3844-5.

Jiang et al., Fundamental studies of tungsten alkylidene imido monoalkoxidepyrrolide complexes. J Am Chem Soc. Jun. 10, 2009;131(22):7770-80.

Jiang et al., Highly Z-selective metathesis homocoupling of terminal olefins. J Am Chem Soc. Nov. 25, 2009;131(46):16630-1.

Kershner et al., $\eta^5$-Heterocyclic metal carbonyls. Coord Chem Rev. 1987;79(1987):279-92.

Kiely et al., Enantioselective synthesis of medium-ring heterocycles, tertiary ethers, and tertiary alcohols by Mo-catalyzed ring-closing metathesis. J Am Chem Soc. Mar. 27, 2002;124(12):2868-9.

Knof et al., Predetermined chirality at metal centers. Angew Chemie Intl Ed. Feb. 1, 1999;38(3):302-22.

Kreickmann et al., Imido alkylidene bispyrrolyl complexes of tungsten. Organometallics. 2007;26: 5702-11.

Lacour et al., Recent developments in chiral anion mediated asymmetric chemistry. Chem Soc Rev. Nov. 2003;32(6):373-82.

Lee et al., Enantioselective synthesis of cyclic enol ethers and all-carbon quaternary stereogenic centers through catalytic asymmetric ring-closing metathesis. J Am Chem Soc. Apr. 19, 2006;128(15):5153-7.

Lee et al., Endo-selective enyne ring-closing metathesis promoted by stereogenic-at-Mo monoalkoxide and monoaryloxide complexes. Efficient synthesis of cyclic dienes not accessible through reactions with Ru carbenes. J Am Chem Soc. Aug. 5, 2009;131(30):10652-61.

Liu et al., Regioselective ring-opening/cross-metathesis reactions of norbornene derivatives with electron-rich olefins. Org Lett. Jan. 6, 2005;7(1):131-3.

Lokare et al., Synthesis, properties, and structure of tethered molybdenum alkylidenes. Organometallics. 2008;27(19):5130-8.

Malcolmson et al., Highly efficient molybdenum-based catalysts for enantioselective alkene metathesis. Nature. Dec. 18, 2008;456(7224):933-7. Epub Nov. 16, 2008.

Marinescu et al., Ethenolysis reactions catalyzed by imido alkylidene monoaryloxide monopyrrolide (MAP) complexes of molybdenum. J Am Chem Soc. Aug. 12, 2009;131(31):10840-1.

Marinescu et al., Inversion of configuration at the metal in diastereomeric imido alkylidene monoaryloxide monopyrrolide complexes of molybdenum. J Am Chem Soc. Jan. 14, 2009;131(1):58-9.

Maruoka et al., Efficient synthesis of sterically hindered chiral binaphthol derivatives. Bull Chem Soc Jpn. 1988;61(8):2975-6.

McDougal et al., Asymmetric Morita-Baylis-Hillman reactions catalyzed by chiral Brønsted acids. J Am Chem Soc. Oct. 8, 2003;125(40):12094-5.

McDougal et al., The development of the asymmetric morita—baylis—hillman reaction catalyzed by chiral brønsted acids. Adv Synth Cat. 2004;346:1231-40.

Meek et al., The significance of degenerate processes to enantioselective olefin metathesis reactions promoted by stereogenic-at-Mo complexes. J Am Chem Soc. Nov. 18, 2009;131(45):16407-9.

Monchaud et al., Ion-pair-mediated asymmetric synthesis of a configurationally stable mononuclear tris(diimine)-iron(II) complex. Angew Chem Int Ed Engl. Jul. 2, 2002;41(13):2317-9.

Pezet et al., Highly diastereoselective preparation of ruthenium bis(diimine) sulfoxide complexes: new concept in the preparation of optically active octahedral ruthenium complexes. Organometallics. 2000;19(20):4008-15.

Poater et al., Understanding d(0)-olefin metathesis catalysts: which metal, which ligands? J Am Chem Soc. Jul. 4, 2007;129(26):8207-16. Epub Jun. 9, 2007.

Rhers et al., A well-defined, silica-supported tungsten imido alkylidene olefin metathesis catalyst. Organometallics. 2006;25(15):3554-7.

Sattely et al., Design and stereoselective preparation of a new class of chiral olefin metathesis catalysts and application to enantioselective synthesis of quebrachamine: catalyst development inspired by natural product synthesis. J Am Chem Soc. Jan. 28, 2009;131(3):943-53.

Sattely et al., Enantioselective synthesis of cyclic amides and amines through mo-catalyzed asymmetric ring-closing metathesis. J Am Chem Soc. Jun. 15, 2005;127(23):8526-33.

Sattely, Cyclic amines and amides through molybdenum-catalyzed asymmetric olefin metathesis: A total synthesis of quebrachamine. Jan. 1, 2007. Boston College Dissertations and Theses. Paper AAI3256831. http://escholarship.bc.edu/dissertations/AAI3256831. 340 pages.

Schrock et al., Further studies of imido alkylidene complexes of tungsten, well-characterized olefin metathesis catalysts with controllable activity. Organometallics. Aug. 1990;9(8):2262-75.

Schrock et al., Molybdenum alkylidyne complexes that contain 3,3'-di-$t$-butyl-5,5', 6,6'-tetramethyl-1, 1'—biphenyl-2,2'—diolate ([Biphen]$^{2-}$) ligand. J Organomet Chem. 2003;684:56-67.

Schrock et al., Molybdenum and tungsten imido alkylidene complexes as efficient olefin-metathesis catalysts. Angew Chem Int Ed Engl. 2003;42(38):4592-33.

Schrock et al., Preparation of molybdenum and tungsten neopentylidyne complexes of the type M(CCMe$_3$)(O$_2$CR)$_3$, their reactions with acetylenes, and the X-ray structure of the $\eta^3$-cyclopropenyl complex W[C$_{3(CMe3)}$Et$_2$]O$_2$CCH$_3$)$_3$$^1$1. Organometallics. 1986;5:25-33.

Schrock et al., Synthesis of molybdenum imido alkylidene complexes and some reactions involving acyclic olefins. J Am Chem Soc. 1990;112:3875-86.

Schrock et al., Thousands of catalysts for olefin metathesis: variability, longevity and asymmetry at the metal. Abstract. Presented Oct. 24, 2008 at Technical University of Berlin.

Schrock, High oxidation state multiple metal-carbon bonds. Chem Rev. 2002;102:145-79.

Schrock, Recent advances in high oxidation state mo and w imido alkylidene chemistry. Chem Rev. 2009;109(8):3211-26.

Schrodi et al., Ruthenium olefin metathesis catalysts for the ethenolysis of renewable feedstocks. Clean: Soil, Air, Water. 2008;36:669-673.

Singh et al., Molybdenum imido alkylidene metathesis catalysts that contain electron-withdrawing biphenolates or binaphtholates. Organometallics. 2007;26(10):2528-39.

Singh et al., Synthesis of monoalkoxide monopyrrolyl complexes Mo(NR)(CHR')(OR")(pyrrolyl): enyne metathesis with high oxidation state catalysts. J Am Chem Soc. Oct. 24, 2007;129(42):12654-5. Epub Sep. 29, 2007.

Sinha et al., Diphenylamido precursors to bisalkoxide molybdenum olefin catalysts. Organometallics. 2006;25(19):4621-6.

Sinha et al., Reactions of M(N-2,6-i-$Pr_2C_6H_3$)(CHR)($CH_2R$ ')$_2$ (M=Mo, W) complexes with alcohols to give olefin metathesis catalysts of the type M(N-2,6-i-$Pr_2C_6H_3$)(CHR)($CH_2R'$)(OR"). Organometallics. 2006;25:1412-23.

Solans-Monfort et al., $d^0$ Re-based olefin metathesis catalysts, Re($\equiv$CR)(=CHR)(X)(Y): The key role of X and Y ligands for efficient active sites. J Am Chem Soc. 2005;127(40):14015-25.

Takano et al., Enantioselective route to both (+)- and (−)-enantiomers of quebrachamine using a single chiral synthon. J Chem Soc Chem Commun. 1981:1153-5.

Takemura et al., Stereochemical aspects of asymmetric Diels-Alder reaction catalyzed by chiral alkoxyaluminum dichlorides. Tetrahedron Lett. 1987;28(46):5687-90.

Tallarico et al., Selectivity in ring-opening metatheses. Tetrahedron. Dec. 1, 1997;53(48):16511-20.

Tayama et al., Activation of ether functionality of allyl vinyl ethers by chiral bis(organoaluminum) Lewis acids: application to asymmetric Claisen rearrangement. Tetrahedron. Oct. 7, 2002;58(41):8307-12.

Tonzetich et al., Reaction of phosphoranes with Mo(N-2,6-i-$Pr_2C_6H_3$)(CHCMe$_3$)[OCMe($CF_3$)$_2$]$_2$: Synthesis and reactivity of an anionic imido alkylidyne complex. Organometallics. 2006;25:4301-6.

Tsai et al, Facile synthesis of trialkoxymolybdenum(VI) alkylidyne complexes for alkyne metathesis. Organometallics. 2000;19:5260-62.

Van Veldhuizen et al., A readily available chiral Ag-based N-heterocyclic carbene complex for use in efficient and highly enantioselective Ru-catalyzed olefin metathesis and Cu-catalyzed allylic alkylation reactions. J Am Chem Soc. May 11, 2005;127(18):6877-82.

Van Veldhuizen et al., A recyclable chiral Ru catalyst for enantioselective olefin metathesis. Efficient catalytic asymmetric ring-opening/cross metathesis in air. J Am Chem Soc. May 8, 2002;124(18):4954-5. Erratum in: J Am Chem Soc. Oct. 15, 2003;125(41):12666.

Walls et al., Alkaloids from stemmadenia species-I : The alkaloids of S. donnell-smithii and S. galeottiana. Tetrahedron. May 1958;2(3-4):173-82.

Weatherhead et al., Mo-catalyzed asymmetric olefin metathesis in target-oriented synthesis: enantioselective synthesis of (+)-africanol. Proc Natl Acad Sci U S A. Apr. 20, 2004;101(16):5805-9. Epub Mar. 31, 2004.

Werner et al., Bur Kennfnie dee asymmetrimhen Kobaltatoms. I. Ber Dtsch Chem Ges. 1911;44:1887-98. German.

Yashiro et al., Efficient stereochemical regulation of octahedral cobalt(III) complexes by a chiral bidentate ligand. Part 2. Remarkable effect of the chelate-ring size in the stereoselective formation of sym-cis-(ethylenediamine-N,N'diacetato)(pentane-2,4-diamine)cobalt(III). J Chem Soc. Dalton Trans. 1994;10:1511-6.

Yashiro et al., Efficient stereochemical regulation of octahedral cobalt(III) complexes by a chiral bidentate ligand. Part 1. Effect of N-alkyl substitutions. J Chem Soc, Dalton Trans. 1994;7:1073-7.

Yi et al., The ruthenium acetylide catalyzed cross-coupling reaction of terminal and internal alkynes: isolation of a catalytically active β-agostic intermediate species. Organometallics. 1998;17(15):3158-60.

Zhang et al., A reductive recycle strategy for the facile synthesis of molybdenum(VI) alkylidyne catalysts for alkyne metathesis. Chem Commun. 2003:832-3.

Zhou et al., Synthesis and reactivity of chiral rhenium indenyl complexes of the formula [($\eta^5$-$C_9H_7$)Re(NO)(PPh3)(X)]n+. Organometallics. 1993;12(10):3918-23.

Zhu et al., Chiral Mo—Binol complexes: activity, synthesis, and structure. efficient enantioselective six-membered ring synthesis through catalytic metathesis. J Am Chem Soc. 1999;121:8251-9.

International Preliminary Report on Patentability from International Patent Application Serial No. PCT/US2007/024318, filed Nov. 21, 2007, mailed May 26, 2009.

International Search Report and Written Opinion in PCT/US2007/024318, issued on May 7, 2008.

International Preliminary Report on Patentability in connection with Application Serial No. PCT/US2009/000465 issued Jul. 27, 2010.

International Search Report and Written Opinion in connection with Application Serial No. PCT/US2009/000465 mailed Jul. 13, 2009.

Invitation to Pay Additional Fees in connection with Application Serial No. PCT/US2009/000465 mailed May 11, 2009.

Bykov et al., "Synthesis of Z-Isomeric Insect Sex Pheromone Components Via Ethenolysis of 1,5-Cyclooctadiene," Tetrahedron 55 (27): 8249-8252 (1999).

Couturier et al., "Metathese Schwefelhaltiger Olefine Mit Einem Metallacyclischen Aryloxo (Chloro)Neopentyliden-Wolfram-Komplex," Angew. Chem. 105 (1): 99-102 (1993).

Feldman et al., "Trigonal-Bipyramidal and Square-Pyramidal Tungstacyclobutane Intermediates are Both Present in Systems in Which Olefins are Metathesized by Complexes of the Type W(CHR') (N-2,6-C6H3-i-Pr2) (OR)2," Organometallics 8: 2266-2268 (1989).

Flook et al., "Z-Selective Olefin Metathesis Processes Catalyzed by a Molybdenum Hexaisopropylterphenoxide Monopyrrolide Complex," J. Am. Chem. Soc. 131: 7962-7963 (2009).

Harrity et al., "Chromenes Through Metal-Catalyzed Reactions of Styrenyl Ethers. Mechanisms and Utility in Synthesis," J. Am. Chem. Soc. 120: 2343-2351 (1998).

Ibrahem et al., "Highly Z- and Enantioselective Ring-Opening/Cross-Metathesis Reactions Catalyzed by Stereogenic-at-Mo Adamantylimido Complexes," J. Am. Chem. Soc. 131 (11): 3844-3845 (2009).

Johannes et al., "Zr-Catalyzed Kinetic Resolution of Allylic Ethers and Mo-Catalyzed Chromene Formation in Synthesis. Enantioselective Total Synthesis of the Antihypertensive Agent (S,R,R,R)—Nebivolol," J. Am Chem Soc. 120: 8340-8347 (1998).

Malcolmson et al., "Highly Efficient Molybdenum-Based Catalysts for Enantioselective Alkene Metathesis," Nature 456 (7224): 933-937 (2008).

Marinescu et al., "Ethenolysis Reactions Catalyzed by Imido Alkylidene Monoaryloxide Monopyrrolide (MAP) Complexes of Molybdenum," J. Am. Chem. Soc. 131: 10840-10841 (2009).

Sattely et al., "Design and Stereoselective Preparation of a New Class of Chiral Olefin Metathesis Catalysts and Application to Enantioselective Synthesis of Quebrachamine: Catalyst Development Inspired by Natural Product Synthesis," J. Am. Chem. Soc. USA 131 (3): 943-953 (2009).

Schaverien et al., "A Well-Characterized, Highly Active, Lewis Acid Free Olefin Metathesis Catalyst," J. Am. Chem. Soc. 108: 2771-2773 (1986).

Stragies et al., "Domino Metathesis—A Combined Ring Opening -, Ring Closing—and Cross Metathesis," Synlett 169-170 (1998).

Wagener et al., "Acyclic Diene Metathesis Depolymerization of Elastomers," Die Makromolekulare Chemie, Rapid Communications 12 (7): 419-425 (1991).

Couturier et al., "Metathesis of Sulfur-Containing Olefins with a Metallacyclic Aryloxo(chloro)neopentylidenetungsten Complex," Angew. Chem. Int. Ed. 32 (1): 112-115, (1993).

International Search Report for PCT/US2010/001949, mailed on Jul. 6, 2011.

Written Opinion for PCT/US2010/001949, mailed on Jul. 6, 2011.

International Preliminary Report on Patentability for PCT/US2010/001949, mailed on Jan. 17, 2012.

English Abstract for EP 1693357-A1, Aug. 23, 2006.

* cited by examiner

CATALYSTS AND PROCESSES FOR THE FORMATION OF TERMINAL OLEFINS BY ETHENOLYSIS

STATEMENT REGARDING FEDERALLY SPONSORED RESEARCH OR DEVELOPMENT

This invention was made with the support under the following government contract CHE-0554734 awarded by the National Science Foundation. The government has certain rights in the invention.

FIELD OF THE INVENTION

The invention related generally to the preparation of terminal olefins by ethenolysis reactions.

BACKGROUND OF THE INVENTION

Carbon-carbon coupling reactions catalyzed by transition metal catalysts are among the most important reactions of organic synthetic chemistry. In particular, ethenolysis reactions allow for the formation of terminal olefins from internal olefins via a cross-metathesis reaction with ethylene. Efficient ethenolysis of natural products comprising internal olefins such as methyl oleate is attractive as a method of obtaining useful chemicals (e.g., comprising terminal olefins) from biomass. Although many transition metal catalysts are known to catalyze ethenolysis reactions, the reactions are generally plagued with problems of moderate to poor conversion and selectively, as well as limited turnover numbers. In particular, selectively of ethenolysis reactions are often low as undesired products are often produced via competing homo-metathesis reactions. Accordingly, improved catalysts and processes are needed.

SUMMARY OF THE INVENTION

The present invention, in some embodiments, provides methods comprising reacting ethylene and a first species comprising at least one internal olefin in the presence of a transition metal catalyst to produce at least one product comprising a double bond, the double bond comprising a carbon atom from the ethylene and an atom of the first species, wherein the at least one product is formed at a turnover number of at least about 5000, a selectivity of at least about 80%, and a conversion of at least about 70%.

The present invention also provides methods comprising providing a catalyst having the structure:

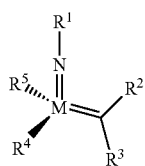

wherein M is Mo or W, $R^1$ is aryl, heteroaryl, alkyl, heteroalkyl, optionally substituted, $R^2$ and $R^3$ can be the same or different and are hydrogen, alkyl, alkenyl, heteroalkyl, heteroalkenyl, aryl, or heteroaryl, optionally substituted, and $R^4$ and $R^5$ can be the same or different and are alkyl, heteroalkyl, aryl, heteroaryl, or silyl, optionally substituted, wherein at least one of $R^4$ or $R^5$ is a ligand containing oxygen bound to M, and reacting ethylene and a first species comprising at least one internal olefin in the presence of the catalyst to produce at least one product comprising a double bond, the double bond comprising a carbon atom from the ethylene and an atom of the first species, wherein the at least one product is formed at a turnover number of at least about 500.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention relates generally to catalysts and processes for the formation of terminal olefin(s) from internal olefin(s) via ethenolysis. Terminal olefins (or alpha-olefins) are important chemicals used as feedstock to produce higher valued end products. Ethenolysis reactions are generally plagued by poor to moderate selectivity, as there usually are competing processes taking place which produce undesired product(s) (e.g., homo- or self-metathesis product(s)). In addition, many catalysts suffer from poor or moderate turnover numbers and/or conversion.

The ethenolysis reactions described herein may proceed with high conversion, high turnover, and/or high selectivity. It is generally believed in the art that during the catalytic cycle of ethenolysis using a transition metal catalyst, a methylidene species (e.g., $M=CH_2$) may form which, in most cases, is highly unstable and prone to bimolecular decomposition, thereby leading to poor turnover numbers, conversion and/or selectivity. However, one set of catalysts described herein has access to methylidene species which are unexpectedly stable and long lived (e.g., observed in solution for at least about 1 minute, at least about 5 minutes, at least about 10 minutes, at least about 20 minutes, at least about 30 minutes, at least about 1 hour, or more) without appreciable decomposition (e.g., less than about 1%, less than about 3%, less than about 5%, less than about 10%, or less than about 20%, etc., decomposition). The unexpected stability of the methylidene species, in combination with the high reactivity of the methylidene species towards olefins, allows for unanticipated success in promoting ethenolysis reactions with high turnover numbers, high selectivity, and/or high conversion.

Figure 1A:
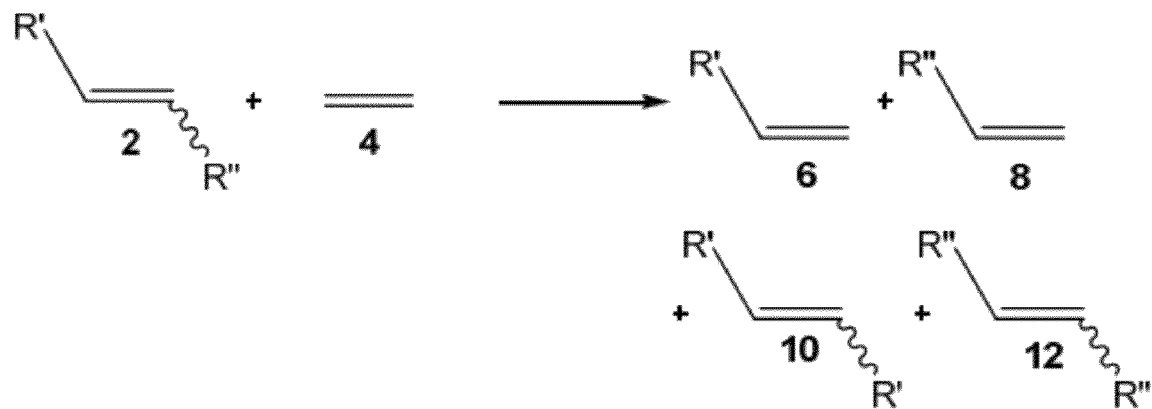
FIG. 1A illustrates an ethenolysis reaction between ethylene and a non-cyclic internal olefin.
Figure 1B:
FIG. 1B illustrates an ethenolysis reaction between ethylene and a cyclic internal olefin.

The term, "ethenolysis," as used herein, refers to a metathesis reaction between ethylene (e.g., a molecule of ethylene) and a species comprising at least one internal olefin (e.g., cyclic or non-cyclic) to produce terminal olefin(s). In some embodiments, an ethenolysis reaction involves reacting ethylene and a species comprising an internal olefin (e.g., in the presence of a transition metal catalyst) to produce at least one product comprising a double bond, the double bond comprising a carbon atom from ethylene and an atom (e.g., a carbon atom) of the first species. The species comprising at least one internal olefin may be substituted and/or comprise heteroatoms. As a non-limiting example, FIG. 1A shows an ethenolysis reaction between a non-cyclic species comprising an internal olefin 2 and ethylene 4 to produce species comprising terminal olefins 6 and 8. Products 10 and 12 are undesired homo- or self-metathesis products (e.g., comprising internal olefins). As another non-limiting example, a cyclic species comprising an internal olefin 14 may react with ethylene to produce corresponding product 18, comprising two terminal olefins, as shown in FIG. 1B.

In some embodiments, the ethenolysis reaction may proceed with good selectivity. The term, "selectivity," as used herein, refers the selectivity of the ethenolysis reaction to form desired product(s) (e.g., terminal olefin(s)) as opposed to undesired product(s) (e.g., homo-metathesis product(s)). In some embodiments, the percent selectivity may be calculated according to the following equation:

$$\% \text{ Selectivity} = 100 \times \left\{ \frac{\text{(moles of desired products(s) produced)}}{\text{(total moles of product(s) produced)}} \right\}$$

wherein the desired products produced in an ethenolysis reaction are the terminal olefin(s) produced (e.g., 6 and 8 in FIG. 1A) and the total products produced include the terminal olefins (e.g., 6 and 8 in FIG. 1A) and any undesired products such as species comprising internal olefins (e.g., homo-metathesis products 10 and 12 in FIG. 1A). The products may be determined using techniques known to those of ordinary skill in the art (e.g., isolation of reagent, GPC, HPLC, NMR, etc.). As a specific example, in the ethenolysis reaction of methyl oleate, the desired products are the terminal olefins (e.g., 1-decene and methyl-9-decenoate) and the undesired products are the homo- or self-metathesis products of 1-decene and methyl-9-decenoate (e.g., 1,18-dimethyl-9-octadecenedioate and 9-octadecene). In some cases, the ethenolysis reaction may proceed with a selectivity of (e.g., the at least one product of the ethenolysis reaction is formed at a selectivity of) at least about 60%, at least about 70%, at least about 75%, at least about 80%, at least about 85%, at least about 90%, at least about 95%, at least about 97%, at least about 98%, at least about 99%, or more. In some cases, the selectivity is about 70%, about 75%, about 80%, about 85%, about 90%, about 95%, about 97%, about 98%, about 99%, or the like. In some instances, the selectivity is between about 60% and about 99%, between about 70% and about 95%, between about 70% and about 90%, or any other range therein.

In some embodiments, the ethenolysis reaction may proceed with good turnover numbers. The term "turnover number," as used herein, refers to the number of average times a catalyst is able to promote an ethenolysis reaction. In some embodiments, the turnover number may be calculated according the following equation:

$$\text{Turnover number} = \% \text{ yield} \times \left\{ \frac{\text{(moles of limiting reagent)}}{\text{(moles of catalyst)}} \right\}$$

wherein the percent yield may be calculated according to the following equation:

$$\% \text{ Yield} = 100 \times \left\{ \frac{\text{(moles of a desired product)}}{\text{(moles of limiting reagent)}} \right\}.$$

The moles of catalyst may be determined from the weight of catalyst (or catalyst precursor) provided, the moles of limiting reagent (e.g., generally the species comprising at least one internal olefin in ethenolysis reactions) may be determined from the amount of limiting reagent added to reaction vessel, and the moles of a desired product (e.g., moles of a terminal olefin produced such as 6 or 8 in FIG. 1A) which may be determined using techniques known to those of ordinary skill in the art (e.g., isolation of product, GPC, HPLC, NMR, etc.). In some cases, the ethenolysis reaction may proceed at a turnover number of (e.g., the at least one product of the ethenolysis reaction is formed at a turnover number of) at least about 500, at least about 1000, at least about 3,000, at least about 5,000, at least about 10,000, at least about 15,000, at least about 20,000, at least about 25,000, at least about 30,000, at least about 40,000, at least about 50,000, or more. In some cases, the turnover number is between about 5,000, and about 50,000, between about 10,000 and about 30,000, between about 15,000 and about 25,000, or any other ranger therein. The turnover frequency is the turnover number divided by the length of reaction time (e.g., seconds).

In some cases, the ethenolysis reaction may proceed with high conversion. Conversion refers to the percent of the limiting reagent converted to product. In some embodiments, percent conversion may be calculated according to the following equation:

$$\% \text{ Conversion} = 100 - \left\{ \frac{\text{(final moles of limiting reagent)} \times 100}{\text{(initial moles of limiting reagent)}} \right\}$$

where the initial moles of the limiting reagent may be calculated from the amount of limiting reagent added to reaction vessel and the final moles of the limiting reagent may be determined using techniques known to those of ordinary skill in the art (e.g., isolation of reagent, GPC, HPLC, NMR, etc.). In some cases, the ethenolysis reaction may proceed with a conversion of (e.g., the at least one product of the ethenolysis reaction is formed at a conversion of) at least about 60%, at least about 70%, at least about 75%, at least about 80%, at least about 85%, at least about 90%, at least about 95%, at least about 97%, at least about 98%, at least about 99%, or more. In some cases, the conversion is about 70%, about 75%, about 80%, about 85%, about 90%, about 95%, about 97%, about 98%, about 99%, or the like. In some instances, the conversion is between about 60% and about 99%, between about 70% and about 95%, between about 70% and about 90%, or any other range therein.

As mentioned above, in some cases, the ethenolysis reaction may proceed with high turnover numbers, high selectivity, and/or high conversion. In a particular embodiment, the reaction may proceed with a turnover number of at least about 5000, a selectivity of at least about 80%, and/or a conversion of at least about 70%, or will a selectivity of at least about 70% and/or a conversion of at least about 80%. In some cases, the reaction may proceed with a turnover number of at least about 15,000, and a selectivity of at least about 85%, and/or a conversion of at least about 60%, or a selectivity of at least about 60% and/or a conversion of at least about 85%. In other cases, the reaction may proceed with a turnover number of at least about 20,000 and a conversion of at least about 50%. It should be understood, however, that any other combination of turnover numbers, conversion, and/or selectivity as described herein, may be obtained.

The ethenolysis reaction may be carried out using techniques known to those of ordinary skill in the art. In some cases, the reaction may involve exposing a catalyst (e.g., as described herein) to a species comprising at least one internal olefin and ethylene (e.g., an atmosphere of ethylene). In some instances, the reaction mixture may be agitated (e.g., stirred, shaken, etc.). The reaction products may be isolated (e.g., via distillation, column chromatography, etc.) and/or analyzed (e.g., gas liquid chromatography, high performance liquid chromatography, nuclear magnetic resonance, etc.) using commonly known techniques.

Species comprising at least one internal olefins will be known to those of ordinary skill in the art. A species comprising at least one internal olefin may be non-cyclic or cyclic, symmetric or non-symmetric, and/or comprise one or more ethylenic units and/or heteroatoms (e.g., oxygen, nitrogen, silicon, sulfur, phosphorus, etc.). Non-limiting examples of species comprising internal olefins are linear alkyl internal olefins such as $C_4$-$C_{30}$ olefins (e.g., 2-hexene, 3-hexene, 2-heptene, 3-heptene, etc.), linear internal heteroalkyl olefins such as methyl oleate (e.g., where the desired products are 1-decene and methyl 9-decenoate), and cycloalkenes such as $C_4$-$C_{30}$ cycloalkenes (e.g., octene (wherein the product is 1,9-decadiene), cyclopentene (wherein the product is 1,6-heptadiene), cyclododecatriene, etc.)

In some cases, the ethenolysis reaction may be carried out under a pressure of ethylene (e.g., in a high pressure vessel, a Fisher-Porter bottle, etc.) of about 1 atm, about 1.5 atm, about 2 atm, about 4 atm, about 6 atm, about 8 atm, about 10 atm, about 20 atm, about 50 atm, about 100 atm, or the like. In some cases, the pressure of ethylene is between about 1 atm and about 10 atm, between about 2 atm and about 5 atm, or the like.

The ethenolysis reaction may be carried out at any suitable temperature. In some cases, the reaction is carried out at about room temperature (e.g., about 25° C., about 20° C., between about 20° C. and about 25° C., or the like). In some cases, however, the reaction may be carried out at a temperature below or above room temperature, for example, at about −70° C., about −50° C., about −30° C., about −10° C., about −0° C., about 10° C., about 30° C., about 40° C., about 50° C., about 60° C., about 70° C., or the like. In some embodiments, the reaction may be carried out at more than one temperature (e.g., reactants added at a first temperature and the reaction mixture agitated at a second wherein the transition from a first temperature to a second temperature may be gradual or rapid.

As noted, one set of catalysts has been identified in accordance with the invention which provides unexpected results in ethenolysis reactions. In some embodiments, the catalyst provided is a metal complex with the structure:

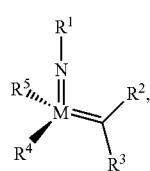

(I)

wherein M is a metal; $R^1$ is aryl, heteroaryl, alkyl, heteroalkyl, optionally substituted; $R^2$ and $R^3$ can be the same or different and are hydrogen, alkyl, alkenyl, heteroalkyl, heteroalkenyl, aryl, or heteroaryl, optionally substituted; and $R^4$ and $R^5$ can the same or different and are alkyl, heteroalkyl, aryl, or heteroaryl, optionally substituted, or $R^4$ and $R^5$ are joined together to form a bidentate ligand with respect to M, optionally substituted. In some cases, at least one of $R^4$ or $R^5$ is a ligand containing oxygen bound to M (e.g., an oxygen-containing ligand) or a ligand containing nitrogen bound to M (e.g., a nitrogen-containing ligand). In some cases, $R^2$ is alkyl. In some instances, M is Mo or W.

In a particular embodiment, one of $R^4$ and $R^5$ is a ligand containing oxygen bound to M (e.g., an oxygen-containing ligand), optionally substituted, and the other is a ligand containing nitrogen bound to M (e.g., a nitrogen-containing ligand), optionally substituted. In some cases, the oxygen-containing ligand and/or the nitrogen-containing ligand may lack a plane of symmetry. In other embodiments, both $R^4$ and $R^5$ are oxygen-containing ligands.

As used herein, the term "oxygen-containing ligand" may be used to refer to ligands comprising at least one oxygen atom capable of coordinating a metal atom (e.g., $R^4$ and/or $R^5$). That is, the term refers to a ligand containing oxygen bound to M. In some cases, the term "oxygen-containing ligand" may also describe ligand precursors comprising at least one hydroxyl group, wherein deprotonation of the hydroxyl group results in a negatively charged oxygen atom, which then coordinates a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center. The oxygen-containing ligand may be chiral or achiral, and/or monodentate or bidentate. A monodentate ligand is a ligand which binds or coordinates the metal center via one coordination site of the metal only, and/or via one site of the ligand only. A bidentate ligand is a ligand which binds or coordinates the metal center via two coordination sites of the metal and/or via two sites of the ligand (e.g., a dialkoxide ligand). Non-limiting of achiral monodentate oxygen-containing ligands include —OC($CH_3$)($CF_3$)$_2$, —OC($CH_3$)$_2$($CF_3$), —OC($CH_3$)$_3$, —OSiPh$_3$, —OAr (Ar=aryl groups such as phenyl, Mes (Mes=2,4,6-Me$_3$C$_6$H$_2$), 2,6-i-Pr$_2$C$_6$H$_3$, HIPT (hexaisopropylterphenyl), TPP (2,3,5,6-Ph$_4$C$_6$H), etc.), and the like.

In some cases, an oxygen-containing ligand may be chiral and may be provided as a racemic mixture or a purified stereoisomer. In some embodiments, the chiral, oxygen-containing ligand may be present in at least 80% optical purity, i.e., the oxygen-containing ligand sample contains 90% of one enantiomer and 10% of the other. In some embodiments, the chiral, oxygen-containing ligand may be at least 90% optically pure, at least 95% optically pure, or, in some cases, at least 99% optically pure.

In some cases, the oxygen-containing ligand (e.g., $R^4$ or $R^5$) lacking a plan of symmetry may comprise the following structure,

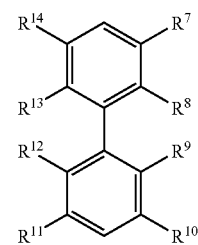

wherein $R^7$ is aryl, heteroaryl, alkyl, or heteroalkyl, optionally substituted; $R^8$ is hydrogen, —OH, halogen, alkyl, heteroalkyl, aryl, heteroaryl, acyl, acyloxy, or —OP, optionally substituted; or, together $R^7$ and $R^8$ are joined to form a ring, optionally substituted; $R^9$ is —OH, —OP, or amino, optionally substituted; $R^{10}$ is hydrogen, halogen, alkyl, heteroalkyl, aryl, heteroaryl, or acyl, optionally substituted; each $R^{11}$, $R^{12}$, $R^{13}$, and $R^{14}$ can be the same or different and is aryl, heteroaryl, alkyl, heteroalkyl, or acyl, optionally substituted; or, together $R^{11}$ and $R^{12}$ are joined to form a ring, optionally substituted; or, together $R^{13}$ and $R^{14}$ are joined to form a ring, optionally substituted; and P is a protecting group. The ring may be an aromatic or a non-aromatic ring. In some embodiments, the ring may be a heterocycle. In some cases, the protecting group may be a Si protecting group (e.g., tert-butyl dimethyl silyl or TBS). In some embodiments, the oxygen-containing ligand may comprise a substituted alkyl group, such as $CF_3$.

In some embodiments, $R^8$ and $R^9$ are attached to the biaryl parent structure via a heteroatom, such as an oxygen atom. For example, $R^8$ and $R^9$ can be —OH, alkoxy, aryloxy, acyloxy, or —OP, where P is a protecting group (e.g., Si protecting group). In some cases, $R^8$ is —OP and $R^9$ is —OH or amino.

Examples of oxygen-containing ligands lacking a plane of symmetry or nitrogen-containing ligands lacking a plane of symmetry may be a group having the structure:

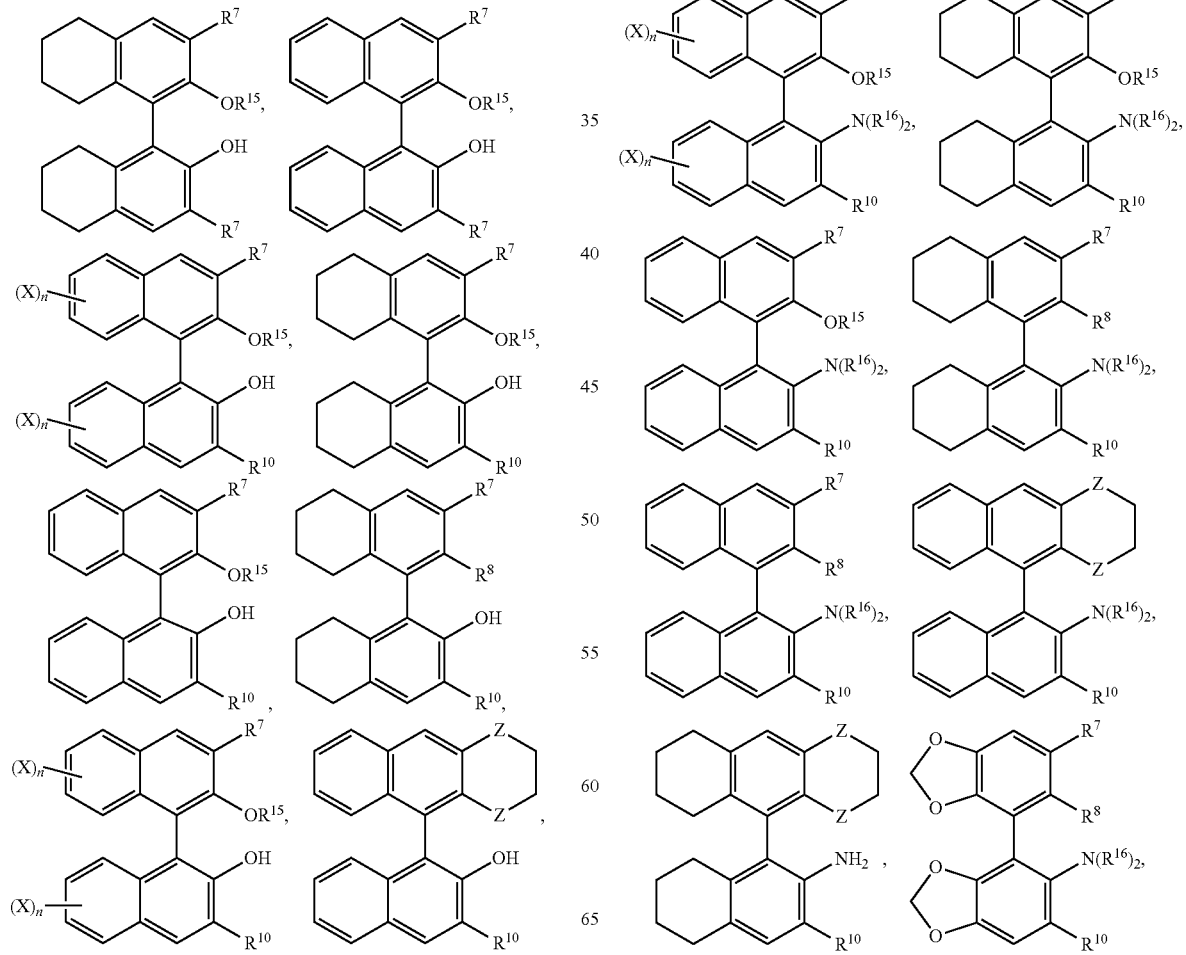

-continued

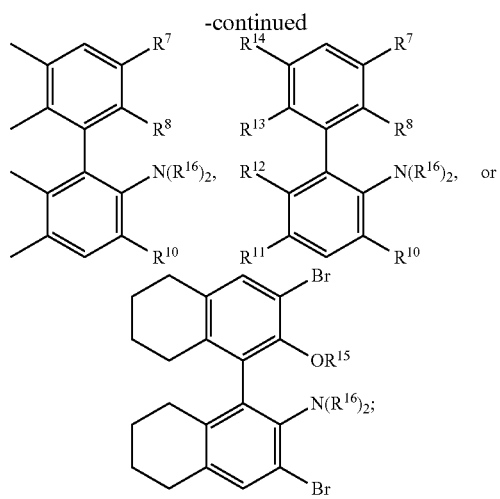

wherein each $R^7$ and $R^8$ can be the same or different and is hydrogen, halogen, alkyl, alkoxy, aryl, acyl, or a protecting group, optionally substituted, $R^{10}$ is hydrogen, halogen, alkyl, heteroalkyl, aryl, heteroaryl, or acyl, optionally substituted, each $R^{11}$, $R^{12}$, $R^{13}$, and $R^{14}$ can be the same or different and is aryl, heteroaryl, alkyl, heteroalkyl, or acyl, optionally substituted, or together $R^{11}$ and $R^{12}$ are joined to form a ring, optionally substituted, or together $R^{13}$ and $R^{14}$ are joined to form a ring, optionally substituted, $R^{15}$ is alkyl, aryl, or a protection group, optionally substituted, $R^{16}$ is hydrogen or an amine protecting group, X may or may not be present and is any non-interfering group, each Z can be the same or different and is $(CH_2)_m$, N, O, optionally substituted, n is 0-5, and m is 1-4. In some embodiments, each $R^7$ and $R^8$ can be the same or different and is hydrogen, halogen, alkyl, alkoxy, aryl, $CF_3$, Si-tri-alkyl, Si-tri-aryl, Si-alkyl-diphenyl, Si-phenyl-dialkyl, or acyl (e.g., ester), optionally substituted; $R^{10}$ is hydrogen, halogen, alkyl, heteroalkyl, aryl, heteroaryl, or acyl, optionally substituted; each $R^{11}$, $R^{12}$, $R^{13}$, and $R^{14}$ can be the same or different and is aryl, heteroaryl, alkyl, heteroalkyl, or acyl, optionally substituted; or, together $R^{11}$ and $R^{12}$ are joined to form a ring, optionally substituted; or, together $R^{13}$ and $R^{14}$ are joined to form a ring, optionally substituted; $R^{15}$ is alkyl, aryl, protecting group Si-trialkyl, Si-triaryl, Si-alkyldiphenyl, Si-phenyldialkyl, or acyl, optionally substituted; $R^{16}$ is hydrogen or an amine protecting group; X can be any non-interfering group; each Z can be the same or different and is $(CH_2)_m$, N, O, optionally substituted; n is 0-5 (or any range therein); and m is 1-4 (or any range therein). In some cases, each $R^7$ and $R^{10}$ is the same or different and is halogen, methyl, t-butyl, $CF_3$, or aryl, optionally substituted.

In one set of embodiments, $R^4$ (or $R^5$) is a monodentate oxygen-containing ligand comprising or lacking a plane of symmetry, or a nitrogen-containing ligand lacking a plane of symmetry; and $R^5$ (or $R^4$) is a nitrogen containing ligand having a plane of symmetry. As used herein, a "nitrogen-containing ligand" (e.g., $R^4$ and/or $R^5$) may be any species capable of binding a metal center via a nitrogen atom. That is, the term refers to a ligand containing nitrogen bound to M. In some cases, the term "nitrogen-containing ligand" may also describe ligand precursors comprising at least one nitrogen group, wherein deprotonation of the nitrogen group results in a negatively charged nitrogen atom, which then coordinates a metal atom. In some instances, the nitrogen atom may be a ring atom of a heteroaryl or heteroalkyl group. In some cases, the nitrogen atom may be a substituted amine group. It should be understood that, in catalyst described herein, the nitrogen-containing ligand may have sufficiently ionic character to coordinate a metal center, such as a Mo or W metal center. Examples of nitrogen-containing ligands (e.g., having a plan of symmetry) include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. In one embodiment, $R^4$ and $R^5$ may be pyrrolyl groups. In some embodiments, the nitrogen-containing ligand may be chiral and may be provided as a racemic mixture or a purified stereoisomer. In some instances, the nitrogen-containing ligand having a plane of symmetry may be a group having the structure:

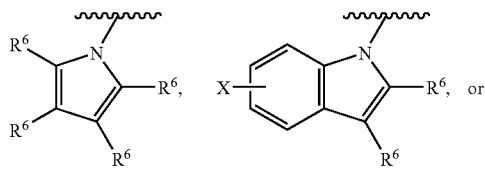

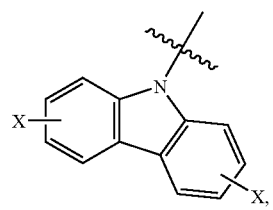

wherein each $R^6$ can be the same or different and is hydrogen, alkyl, heteroalkyl, aryl, heteroaryl, optionally substituted; and X may be present or absent and is any non-interfering group. As used herein, the term "non-interfering group," refers to any group (e.g., an organic group or permissible substituent to an organic group) which does not significantly effect or alter the properties (e.g., catalytic activity, solubility, etc.) of the compound.

In some embodiments, the catalyst may comprise one of the following structures:

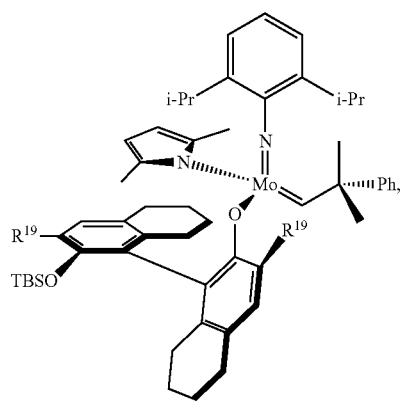

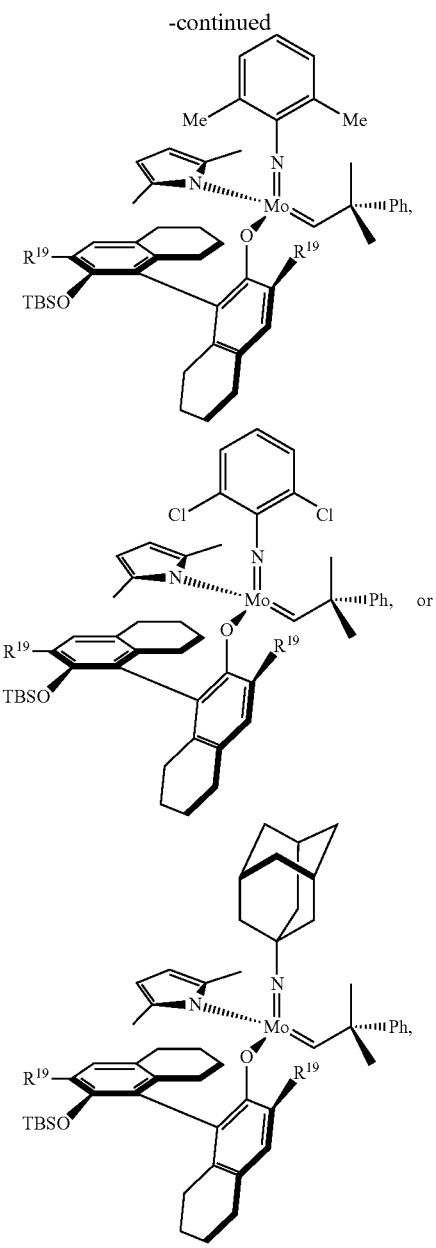

wherein $R^{19}$ is F, Cl, Br, or I.

In some cases, $R^1$ may be linked to form a ring with $R^2$ or $R^3$. For example, the metal complex may comprise $R^1$ linked to form a ring with $R^2$ or $R^3$ prior to use as a catalyst, and, upon initiation of the catalyst in a metathesis reaction, the linkage between $R^1$ and $R^2$ or $R^3$ may be broken, therefore rendering each of the ligands monodentate. The ring may comprise any number of carbon atoms and/or heteroatoms. In some cases, the cyclic olefin may comprise more than one ring. The ring may comprise at least 4, at least 5, at least 6, at least 7, at least 8, at least 9, at least 10, or more, atoms.

In some cases, $R^4$ and $R^5$ are joined together to form a chiral, bidentate ligand. In some cases, the ligand may be of at least 80% optical purity. Examples of chiral bidentate ligands include biphenolates and binaphtholates, optionally substituted with alkyl, alkenyl, alkynyl, cycloalkyl, cycloalkenyl, cycloalkynyl, aryl, alkaryl, aralkyl, optionally interrupted or terminated by heteroatoms, carbonyl groups, cyano, $NO_2$, alkoxy, aryloxy, hydroxy, amino, thioalkyl, thioaryl, sulfur-containing groups, halides, substituted derivatives thereof, and the like. In some cases, the chiral, bidentate ligand may be substituted at positions in proximity of the metal center to impart stereoselectivity to the reactive site of the catalyst.

Catalysts and/or catalyst precursors of the invention may comprise substituted imido groups (e.g., $N—R^1$). Without wishing to be bound by theory, the imido group may stabilize the organometallic compositions described herein by providing steric protection and/or reducing the potential for bimolecular decomposition. In some embodiments, $R^1$ may be aryl, heteroaryl, alkyl, or heteroalkyl, optionally substituted. In some cases, $R_1$ is aryl or alkyl. In some cases, $R^1$ may be selected to be sterically large or bulky, including phenyl groups, substituted phenyl groups (e.g., 2,6-disubstituted phenyls, 2,4,6-trisubstituted phenyls), polycyclic groups (e.g., adamantyl), or other sterically large groups. In some embodiments, $R^1$ may be 2,6-dialkylphenyl, such as 2,6-diisopropylphenyl. For example, in some embodiments, $R^1$ is

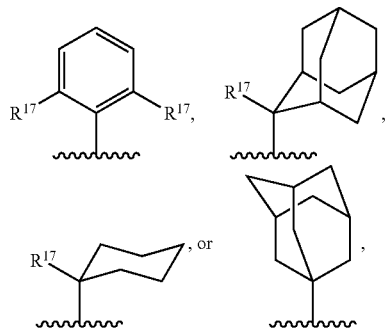

wherein each $R^{17}$ can be the same or different and is hydrogen, halogen, alkyl, heteroalkyl (e.g., alkoxy), aryl, acyl, or —OP, optionally substituted, where P is a protecting group.

In some embodiments, $R^1$ is

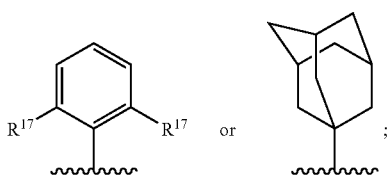

$R^2$ is $CMe_2Ph$ or $CMe_3$; and $R^4$ is an enantiomer of the following structure,

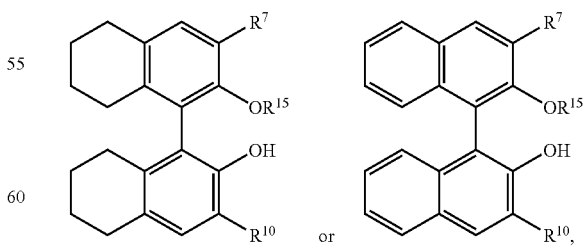

wherein each $R^{17}$ is the same or different and is halogen, methyl, t-butyl, $CF_3$, or aryl, optionally substituted, $R^5$ is a nitrogen-containing ligand having a plane of symmetry, and $R^7$, $R^{10}$, and $R^{15}$ are as described herein.

Catalysts and/or catalyst precursors of the invention may further comprise substituted alkylidene groups (e.g., $CR^2R^3$). The alkylidene groups may be mono-substituted (e.g., one of $R^2$ and $R^3$ is hydrogen) or di-substituted with, for example, alkyl, heteroalkyl, aryl, or heteroaryl groups, optionally substituted. In some cases, the alkylidene may be mono-substituted with, for example, t-butyl, dimethylphenyl, or the like. In some cases, $R^2$ is $CMe_2Ph$ or $CMe_3$, and $R^3$ is hydrogen.

In some cases, catalysts comprising one or more sterically large ligands may be synthesized. For example, at least one of $R^1$-$R^5$ may contain sterically large groups, such as tert-butyl, isopropyl, phenyl, naphthyl, adamantyl, substituted derivatives thereof, and the like. Sterically large ligands may also include ligands comprising substituents positioned in close proximity to the metal center when the ligand is bound to the metal.

In some cases, the catalyst comprises a stereogenic metal atom. As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In a particular embodiment, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral, molecular product.

In some cases, when the catalyst comprises a stereogenic metal atom, and two or more ligands that bind the metal atom, each ligand associated with the metal complex comprises an organic group. The ligands may be monodentate ligands, i.e., the ligands bind the stereogenic metal atom via one site of the ligand (e.g., a carbon atom or a heteroatom of the ligand). In some cases, a monodentate ligand may bind the metal center via a single bond or a multiple bond. In some cases, the metal complex comprises at least one ligand lacking a plane of symmetry. That is, at least one ligand bound to the stereogenic metal atom is a chiral ligand. In some cases, the metal complex comprises an oxygen-containing ligand, including chiral and/or achiral oxygen-containing ligands. In some cases, the metal complex comprises a nitrogen-containing ligand, including chiral and/or achiral nitrogen-containing ligands. For example, the ligand may be a chiral or achiral nitrogen heterocycle, such as a pyrrolide. In some cases, the metal atom may be bound to at least one carbon atom. In some embodiments, the catalyst comprises the metal complex in a diastereomeric ratio greater than 1:1, greater than about 5:1, greater than about 7:1, greater than about 10:1, greater than about 20:1, or, in some cases, greater.

As suitable, the catalysts employed in the present invention may involve the use of metals which can mediate a particular desired chemical reaction. In general, any transition metal (e.g., having d electrons) may be used to form the catalyst, e.g., a metal selected from one of Groups 3-12 of the periodic table or from the lanthanide series.

However, in some embodiments, the metal may be selected from Groups 3-8, or, in some cases, from Groups 4-7. In some embodiments, the metal may be selected from Group 6. According to the conventions used herein, the term "Group 6" refers to the transition metal group comprising chromium, molybdenum, and tungsten. In some cases, the metal is molybdenum or tungsten. In some embodiments, the metal is not ruthenium. It may be expected that these catalysts will perform similarly because they are known to undergo similar reactions, such as metathesis reactions. However, the different ligands are thought to modify the catalyst performance by, for example, modifying reactivity, and preventing undesirable side reactions. In a particular embodiment, the catalyst comprises molybdenum. Additionally, the present invention may also include the formation of heterogeneous catalysts containing forms of these elements.

In some cases, a catalyst may be a Lewis base adduct. The terms "Lewis base" and "Lewis base adduct" are known in the art and refer to a chemical moiety capable of donating a pair of electrons to another chemical moiety. For example, the metal complex may be combined with tetrahydrofuran (THF), wherein at least one THF molecules coordinate the metal center to form a Lewis base adduct. In some cases, the Lewis base adduct may be $PMe_3$. In some embodiments, the catalyst may be formed and stored as a Lewis base adduct, and may be "activated" in a subsequent reaction step to restore the catalyst that does not comprise a Lewis base adduct.

Those of ordinary skill in the art will be aware of methods to synthesize catalysts described herein for use in an ethenolysis reaction. The catalysts may be isolated, or may be formed in situ and utilized in a subsequent reaction (e.g. one-pot reaction). The term "one-pot" reaction is known in the art and refers to a chemical reaction which can produce a product in one step which may otherwise have required a multiple-step synthesis, and/or a chemical reaction comprising a series of steps that may be performed in a single reaction vessel. One-pot procedures may eliminate the need for isolation (e.g., purification) of catalysts and/or intermediates, while reducing the number of synthetic steps and the production of waste materials (e.g., solvents, impurities). Additionally, the time and cost required to synthesize catalysts and/or other products may be reduced. In some embodiments, a one-pot synthesis may comprise simultaneous addition of at least some components of the reaction to a single reaction chamber. In one embodiment, the one-pot synthesis may comprise sequential addition of various reagents to a single reaction chamber.

In some embodiments, a catalyst having the structure (I) where M is M or W may be prepared according to the following procedure. Molybdate or tungstate, for example ammonium molybdate (e.g., $(NH_4)_2Mo_2O_7$), alkylammonium molybdate (e.g., $[Mo_8O_{26}][CH_3N(C_8H_{17})_3]_4$, $[Mo_8O_{26}][HN(C_{12}H_{25})_3]_4$), or their equivalent, may be combined under an inert atmosphere with amine of the general formula $NHXR^1$, where $R^1$ is as defined herein, and where X is hydrogen or trimethylsilyl (e.g., $(CH_3)_3SiNHAr$, where Ar is an aryl or heteroaryl group). A compound capable of deprotonating $NHXR^1$, for example, triethylamine, pyridine, substituted pyridine or other equivalent nitrogen bases and halogenating or triflating agents (e.g., $Me_3SiCl$, $Me_3SiBr$, $Me_3SiSO_3CF_3$ or their equivalent) may be added to the reaction mixture. A suitable solvent may be employed which may or may not contain an equivalent amount of coordinating Lewis base (e.g., 1,2-dimethoxyethane (DME), tetrahydrofuran (THF), pyridine, quinuclidine, $(R)_2PCH_2CH_2P(R)_2$, and $P(R)_3$ where R=alkyl, aryl), and the reaction mixture may be heated to approximately 60-70° C. for at least about 6 hours under an inert atmosphere (e.g., a nitrogen atmosphere), thereby yielding $Mo(NR^1)_2(halogen)_2(Lewis base)_x$ where x is 0, 1 or 2.

The reaction product may be retained in solution or isolated as a solid by the evaporation of the volatile components from solution using distillation techniques. Treatment of the compound with two equivalents of a Grignard or lithium reagent (or equivalent), such as $ClMgCHR^2R^3$, may lead to the production of an intermediate, having the general formula $M(NR^1)_2(CHR^2R^3)_2$, where $R^1$, $R^2$ and $R^3$ have been previously defined. This complex may then be treated with three equivalents of a strong acid, such as triflic acid ($HOSO_2CF_3$), in 1,2-dimethoxyethane (DME, or other suitable solvent), thereby generating a six coordinate complex, $M(NR^1)(CR^2R^3)(OSO_2CF_3)_2 \cdot (DME)$ (or other equivalent). One equivalents of $YR^4$ and $YR^5$ (where $R^4$ and $R^5$ are as previously defined and Y is H, Li, Na, K, etc.) or two equivalents of $YR^4$ (when $R^4$ and $R^5$ are the same) or one equivalent of a bidentate ligand (when $R^4$ and $R^5$ are joined together to form a bidentate ligands) may be reacted with this complex to yield a catalyst having a structure $M(NR^1)(CR^2R^3)(R^4)(R^5)$.

In some embodiments, the catalyst may be formed and isolated or generated in situ from a catalyst precursor having the strcture (II)

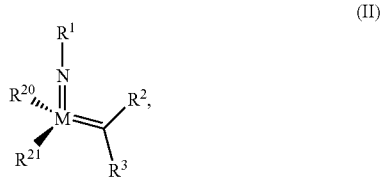

(II)

wherein M is Mo or W; $R^1$ is alkyl, heteroalkyl, aryl, or heteroaryl, optionally substituted; $R^2$ and $R^3$ can be the same or different and are hydrogen, alkyl, alkenyl, heteroalkyl, heteroalkenyl, aryl, or heteroaryl, optionally substituted; $R^{20}$ and $R^{21}$ can be the same or different and are heteroalkyl or heteroaryl, optionally substituted, or $R^{20}$ and $R^{21}$ are joined together to form a bidentate ligand with respect to M, optionally substituted; and wherein $R^{20}$ and $R^{21}$ each comprise at least one nitrogen atom (e.g., are nitrogen-containing ligands). In some cases, $R^{20}$ and $R^{21}$ each coordinate M via a nitrogen atom. For example, $R^{20}$ and $R^{21}$ may both be pyrrolyl groups which coordinate the metal via the nitrogen atoms of the pyrrolyl ring. The nitrogen-containing ligand may be selected to interact with an oxygen-containing ligand such that an oxygen-containing ligand can readily replace an nitrogen-containing ligand to generate the catalyst.

As shown by the illustrative embodiment in Scheme 1, a catalyst may be formed from catalyst precursor (II) by reacting the catalyst precursor with an oxygen-containing ligand (e.g., $R^4$ and $R^5$) such that the oxygen-containing ligand replaces $R^{20}$ and $R^{21}$ to form the catalyst having the structure (III), wherein $R^{20}$ and $R^{21}$, in protonated or non-protonated form, may be released. $R^4$ and $R^5$ may be oxygen-containing ligands or $R^4$ and $R^5$ may be joined together to form a bidentate, oxygen-containing ligand. In some embodiments, only one of $R^{20}$ or $R^{21}$ is reacted with an oxygen-containing ligand to form a catalyst, for example, having the structure (IV) or (V), as shown in Scheme I.

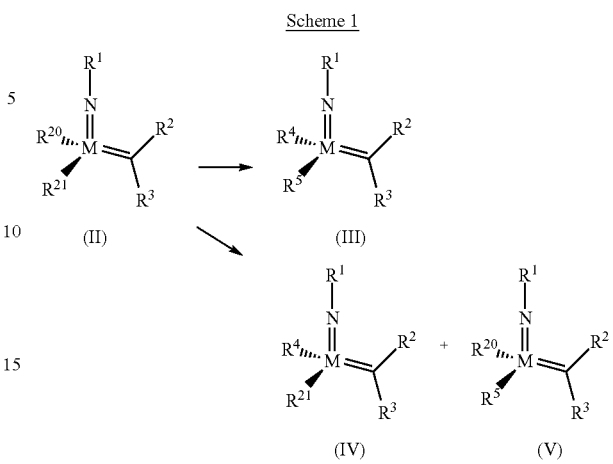

Scheme 1

In some cases, the oxygen-containing ligand may be in a protonated form prior to coordinating the metal center, and may then have sufficiently ionic character (e.g., may be deprotonated) upon coordination to the metal center. Similarly, the nitrogen-containing ligand may be in a deprotonated form when bound to the metal center, and may become protonated upon release from the metal center. For example, $R^{20}$ and $R^{21}$ may be pyrrolyl groups coordinating the metal center such that, upon exposure of the catalyst precursor to an oxygen-containing ligand such as biphenolate, the biphenolate ligand may replace the pyrrolyl groups to form the catalyst, resulting in the release of two equivalents of pyrrole. Ligands of the present invention may be described using nomenclature consistent with their protonated or deprotonated forms, and, in each case, it should be understood that the ligand will adopt the appropriate form to achieve its function as, for example, either a ligand bound to a metal center or an inert species in the reaction mixture. For example, in an illustrative embodiment, the term "pyrrolyl" may be used to describe a deprotonated, anionic pyrrole group which may coordinate a metal center, while the term "pyrrole" may be used to describe a neutral pyrrole group which does not coordinate the metal center but may be present in solution as an inert species that does not react with other components in the reaction mixture.

In cases where the catalyst may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. That is, $R^{20}$ and $R^{21}$ may be selected such that the released $R^{20}$ and/or $R^{21}$ groups may not interfere with subsequent reactions that may involve the catalyst or may not react with any other species in the reaction. In some cases, the $R^{20}$ and $R^{21}$ groups may be released in protonated form (e.g., H—$R^{20}$ and H—$R^{21}$, or $H_2(R^{20}$-$R^{21})$) but may be similarly inert to other species or reagents, including those involved in subsequent reactions. Those of ordinary skill in the art would be able to select the appropriate nitrogen-containing ligand(s) (e.g., $R^{20}$ and $R^{21}$) suitable for use in a particular application, e.g., such that the released nitrogen-containing ligand(s) do not contain carbon-carbon double bonds which may react with the generated olefin metathesis catalyst.

In some embodiments, a catalyst comprising a stereogenic metal center may be produced by reacting an organometallic composition (e.g., a catalyst precursor) having a plane of symmetry with a monodentate ligand lacking a plane of symmetry, to produce a catalyst comprising a stereogenic metal atom. In some cases the method may comprise reacting a racemic mixture of an organometallic composition comprising a stereogenic metal center with a monodentate ligand lacking a plane of symmetry, to produce a metal complex comprising a stereogenic metal atom. The metal complex may comprise two or more ligands, wherein each ligand binds the stereogenic metal atom via one bond, i.e., each ligand is a monodentate ligand. In some cases, the method may comprise providing a catalyst precursor comprising an organometallic composition having a plane of symmetry and including two or more ligands, in a reaction vessel. At least one ligand may be replaced by a monodentate ligand (e.g., oxygen-containing or nitrogen-containing ligand), thereby synthesizing a metal complex comprising the stereogenic metal atom.

In some cases, the methods described herein may be performed in the absence of solvent (e.g., neat). In some cases, the methods may comprise one or more solvents. Examples of solvents that may be suitable for use in the invention include, but are not limited to, benzene, p-cresol, toluene, xylene, mesitylene, diethyl ether, glycol, petroleum ether, hexane, cyclohexane, pentane, dichloromethane (or methylene chloride), chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like.

As used herein, the term "reacting" refers to the formation of a bond between two or more components to produce a compound. In some cases, the compound is isolated. In some cases, the compound is not isolated and is formed in situ. For example, a first component and a second component may react to form one reaction product comprising the first component and the second component joined by a covalent bond (e.g., a bond formed between a ligand and a metal, or a bond formed between two substrates in a metathesis reaction). That is, the term "reacting" does not refer to the interaction of solvents, catalysts, bases, ligands, or other materials which may serve to promote the occurrence of the reaction with the component(s).

As used herein, the term "organic group" refers to any group comprising at least one carbon-carbon bond and/or carbon-hydrogen bond. For example, organic groups include alkyl groups, aryl groups, acyl groups, and the like. In some cases, the organic group may comprise one or more heteroatoms, such as heteroalkyl or heteroaryl groups. The organic group may also include organometallic groups. Examples of groups that are not organic groups include —NO or —N$_2$. The organic groups may be optionally substituted, as described below.

The term "organometallic" is given its ordinary meaning in the art and refers to compositions comprising at least one metal atom bound to one or more than one organic ligands. In some cases, an organometallic compound may comprise a metal atom bound to at least one carbon atom.

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

The phrase "protecting group" as used herein refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (e.g., see Greene, T. W.; Wuts, P. G. M. *Protective Groups in Organic Synthesis*, 2$^{nd}$ ed.; Wiley: New York, 1991).

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. In some embodiments, an alkyl group may be a lower alkyl group, wherein a lower alkyl group comprises 10 or fewer carbon atoms in its backbone (e.g., $C_1$-$C_{10}$ for straight chain lower alkyls).

The term "heteroalkyl" is given its ordinary meaning in the art and refers to alkyl groups as described herein in which one or more atoms is a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls, and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the aryl groups may include monocyclic carbocyclic aryl groups and polycyclic or fused compounds (e.g., two or more adjacent ring atoms are common to two adjoining rings) such as naphthyl group. Non-limiting examples of aryl groups include phenyl, naphthyl, tetrahydronaphthyl, indanyl, indenyl, and the like. The term "heteroaryl" is given its ordinary meaning in the art and refers to aryl groups as described herein in which one or more atoms is a heteroatom (e.g., oxygen, nitrogen, sulfur, and the like), optionally substituted. Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like.

It will also be appreciated that aryl and heteroaryl moieties, as defined herein, may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)-heteroaryl moieties. Thus, as used herein, the phrases "aryl or heteroaryl" and "aryl, heteroaryl, (aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl" are interchangeable.

The term "olefin," as used herein, refers to any species having at least one ethylenic double bond such as normal and branched chain aliphatic olefins, cycloaliphatic olefins, aryl substituted olefins and the like. Olefins may comprise terminal double bond(s) ("terminal olefin") and/or internal double bond(s) ("internal olefin") and can be cyclic or acyclic, linear or branched, optionally substituted. The total number of carbon atoms can be from 1 to 100, or from 1 to 40; the double bonds may be unsubstituted or mono-, bi-, tri- or tetrasubstituted.

The term "cyclic olefin," as used herein, refers to any cyclic species comprising at least one ethylenic double bond in a ring. The atoms of the ring may be optionally substituted. The ring may comprise any number of carbon atoms and/or heteroatoms. In some cases, the cyclic olefin may comprise more than one ring. A ring may comprise at least 3, at least 4, at least 5, at least 6, at least 7, at least 8, or more, atoms. Non-limiting examples of cyclic olefins include norbornene, dicyclopentadiene, bicyclo compounds, oxabicyclo compounds, and the like, all optionally substituted. "Bicyclo compounds" are a class of compounds consisting of two rings only, having two or more atoms in common. "Oxabicyclo compounds" are a class of compounds consisting of two rings only, having two or more atoms in common, wherein at least one ring comprises an oxygen atom.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "halogen" or "halide" designates —F, —Cl, —Br, or —I.

The term "alkoxy" refers to the group, —O-alkyl.
The term "aryloxy" refers to the group, —O-aryl.
The term "acyloxy" refers to the group, —O-acyl.
The term "arylalkyl," as used herein, refers to an alkyl group substituted with an aryl group.

The terms "amine" and "amino" are art-recognized and refer to both unsubstituted and substituted amines, e.g., a moiety that can be represented by the general formula: N(R')(R")(R''') wherein R', R", and R''' each independently represent a group permitted by the rules of valence.

The term "dialkyl amine" is art-recognized and can be represented by the general formula: N(R')(R")⁻, wherein R' and R" are alkyl groups.

An "alkoxide" ligand herein refers to a ligand prepared from an alcohol, in that removing the hydroxyl proton from an alcohol results in a negatively charged alkoxide.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For example, a substituted alkyl group may be $CF_3$. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

EXAMPLE 1

The following example describes the use of a series of catalysts for ethenolysis reactions.

MonoAryloxide-Pyrrolide (MAP) olefin metathesis catalysts 1 and 2 (shown in FIG. 2) can be prepared through addition of a phenol to a bispyrrolide species. In the process of studying related tungsten MAP complexes, it was noticed that some methylidene species were unusually stable, yet highly reactive. For example, a 0.04 M solution of W(NAr)(CH$_2$)(O-2,3,5,6-Ph$_4$C$_6$H)(Me$_2$Pyr) (Me$_2$Pyr=2,5-dimethylpyrrolide) in toluene-d$^8$ could be heated to 80° C. without causing significant decomposition in a period of ~1 hour. The stability of methylidene species is likely to be an important feature of MAP species that are especially efficient in a reaction in which ethylene is present. Without wishing to be bound by theory, the long-lived, reactive methylidene species and lability of unsubstituted metallacyclobutane intermediates suggest that efficient ethenolysis of internal linear or cyclic olefins may be possible. Efficient ethenolysis of natural products such as methyl oleate is attractive as a method of obtaining useful chemicals from biomass.

Figure 2:
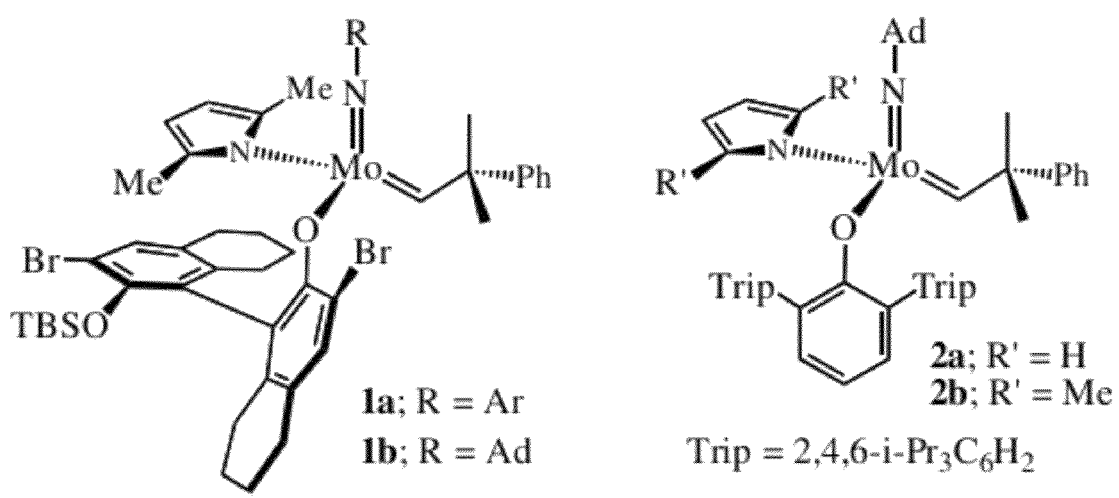
FIG. 2 shows non-limiting examples of catalysts for ethenolysis, according to some embodiments of the present invention.
Figure 3:
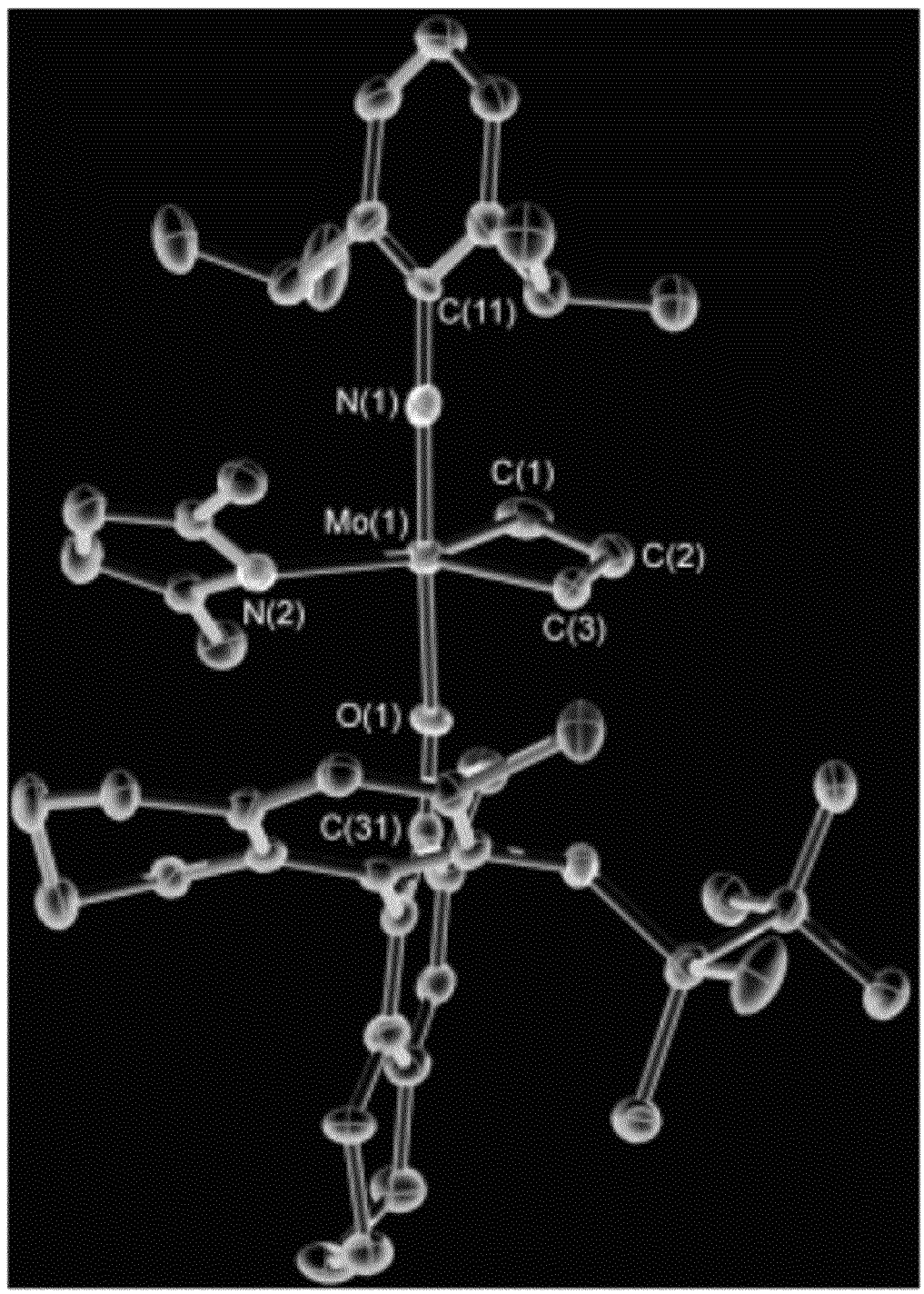
FIG. 3 shows the x-ray crystal structure of a catalyst for ethenolysis reaction, according to a non-limiting embodiment of the present invention.

In this non-limiting example, exposure of catalyst 1a Mo(NAr)(CHC(CH$_3$)$_2$Ph))(Me$_2$Pyr)(OBitet), shown in FIG. 2) to 1 atm of ethylene has been shown to lead to mixtures that contain the two diastereomers of 1a, the two diastereomers of Mo(NAr)(CH$_2$)(Me$_2$Pyr)(OBitet), the unsubstituted molybdacyclobutane, Mo(NAr)(CH$_2$CH$_2$CH$_2$)(Me$_2$Pyr)(OBitet), and CH$_2$=CHCMe$_2$Ph, along with ethylene (OBitet is the aryloxide shown in FIG. 2 in compound 1a). A reaction between Mo(NAr)(CHCMe$_3$)(Me$_2$Pyr)(OBitet) and ethylene resulted in the formation of a molybdacyclobutane complex, Mo(NAr)(CH$_2$CH$_2$CH$_2$)(Me$_2$Pyr)(OBitet). The complex was isolated at –30° C. in the presence of ethylene (1 atm). An X-ray structural study reveals it to have the trigonal bipyramid (TBP) structure shown in FIG. 3, one that is virtually identical to the structure found for W(NAr)(CH$_2$CH$_2$CH$_2$)(Me$_2$Pyr)(OBitet). Specifically, FIG. 3 shows the POV-ray drawing of Mo(NAr)(C$_3$H$_6$)(Me$_2$Pyr)(OBitet). Thermal ellipsoids are displayed at 50% probability level. Hydrogen atoms were omitted for clarity. Molybdacyclobutane species are especially rare because they lose an olefin readily. To the best of the inventor's knowledge only one other molybdacyclobutane, a square pyramidal bis-t-butoxide species, has been structurally characterized. Metallacyclobutanes that have a TBP structure are proposed to lose an olefin more readily than a SP species. Mo(NAr)(CH$_2$CH$_2$CH$_2$)(Me$_2$Pyr)(OBitet) releases ethylene readily when an ethylene atmosphere is removed to give mixtures of the two diastereomers of Mo(NAr)(CH2)(Me$_2$Pyr)(OBitet). In some cases, the two diastereomers of Mo(NAr)(CH$_2$)(Me$_2$Pyr)(OBitet) were observed to decompose in the absence of ethylene over a period of 1-2 days.

Ethenolysis (employing 99.5% pure ethylene) of methyl oleate (Table 1) initiated by 1a at room temperature yielded essentially only 1-decene (1D) and methyl-9-decenoate (M9D) with a selectivity of >99% and yields up to 95% (entries 1-4). (The other possible products are 1,18-dimethyl-9-octadecenedioate and 9-octadecene.) The highest turnovers are found at the higher pressures (see entries 3 and 4). Without wishing to be bound by theory, all results may be consistent with time dependent catalyst decomposition and a (low) solubility of ethylene in methyl oleate that limits conversion at low pressures. The catalysts shown in entries 5-7 produce product with lower selectivities and yields. An OBitet catalyst that contains the adamantylimido ligand (1b, entry 8) is almost as successful as 1a.

In Table 1, (a) Conversion was calculated by=100−[(final moles of MO)×100/(initial moles of MO)]; (b) Selectivity was calculated by=(1D+M9D)×100/(total products); (c) Yield was calculated by=(1D or M9D)×100/(initial moles of MO); and TON was calculated by=percent yield[(moles of MO)/(moles catalyst)]. Abbreviations: Ar=2,6-i-Pr$_2$C$_6$H$_3$; Ad=1-adamantyl; HIPTO=hexaisopropylterphenoxide; TPP=2,3,5,6-Ph$_4$C$_6$H; Me$_2$Pyr=2,5-dimethylpyrrolide; and Bitet is the aryl group shown in FIG. 2 in compound 1a.

Tungstacyclobutane catalysts (entries 9 and 10) produced results that were inferior to molybdenum catalysts in yield, either at room temperature or at 50° C., although selectivity was still >99%. Without wishing to be bound by theory, since it is likely that the rate limiting step in ethenolysis is loss of ethylene from an unsubstituted metallacyclobutane, one possible reason why tungsten is slower than molybdenum is that tungstacyclobutanes release ethylene more slowly than molybdacyclobutanes. Another possibility is that the ester carbonyl binds to tungsten more strongly than it does to molybdenum and inhibits turnover to a more significant degree.

Ethenolysis of 30000 equiv of cyclooctene to give 1,9-decadiene with 1a as the catalyst proceeded with a TON of 22500 (75% yield) at 20 atm (Table 2). Initiation of polymerization of cyclooctene with 1a may be slow, so little 1a is consumed before it reacts with ethylene to yield Mo(NAr)(CH$_2$)(Me$_2$Pyr)(OBitet), and ethenolysis then proceeds rapidly. At 1 atm of ethylene in an NMR scale reaction, poly(cyclooctene) is observed, but the amount of polymer decreases substantially upon addition of more ethylene. Essentially the same result as shown in entry 5 was observed when commercial 99.995% ethylene was employed. Therefore impurities in ethylene do not appear to limit TON.

TABLE 1

Ethenolysis of methyl oleate (MO).

| Entry | Catalyst | Eq. | P (atm) | Time (h) | % Conv.[a] | % Select.[b] | % Yield[c] | TON[d] |
|---|---|---|---|---|---|---|---|---|
| 1 | Mo(NAr)(CHCMe$_2$Ph)(Me$_2$pyr)(OBitet) (1a) | 500 | 4 | 1 | 94 | >99 | 94 | 470 |
| 2 | 1a | 1000 | 4 | 20 | 80 | >99 | 80 | 800 |
| 3 | 1a | 5000 | 4 | 15 or 48 | 58 | >99 | 58 | 2900 |
| 4 | 1a | 5000 | 10 | 15 | 95 | >99 | 95 | 4750 |
| 5 | Mo(NAr)(CHCMe$_2$Ph)[OCMe(CF$_3$)$_2$]$_2$ | 500 | 4 | 2 | 83 | 76 | 63 | 315 |
| 6 | Mo(NAr)(CHCMe$_2$Ph)(Me$_2$pyr)(TPP) | 500 | 4 | 20 | 87 | 86 | 75 | 325 |
| 7 | Mo(NAr)(CHCMe$_2$Ph)(Me$_2$pyr)(OSiPh$_3$) | 500 | 4 | 1 | 86 | 92 | 79 | 395 |
| 8 | Mo(NAd)(CHCMe$_2$Ph)(Me$_2$pyr)(OBitet) (1b) | 500 | 4 | 18 | 96 | 98 | 94 | 470 |
| 9 | W(NAr)(C$_3$H$_6$)(Me$_2$pyr)(OBitet) | 500 | 4 | 17 | 48 | >99 | 48 | 240 |
| 10 | W(NAr)(C$_3$H$_6$)(Me$_2$pyr)(OBitet) (50° C.) | 500 | 4 | 4 | 18 | >99 | 62 | 310 |

TABLE 2

Ethenolysis of cyclooctene with 1a.

| Entry | Equiv. | P (atm) | Time (hr) | % Conv. | % Yield | % Select. | TON |
|---|---|---|---|---|---|---|---|
| 1 | 5000 | 10 | 16 | 98 | 90 | 92 | 4500 |
| 2 | 10000 | 10 | 20 | 98 | 80 | 82 | 8000 |
| 3 | 10000 | 20 | 20 | 93 | 93 | >99 | 9300 |
| 4 | 20000 | 20 | 16 | 88 | 88 | >99 | 17600 |
| 5 | 30000 | 20 | 20 | 75 | 75 | >99 | 22500 |

Ethenolysis of 5000 equivalents of cyclopentene at 20 atm of 99.5% ethylene leads to 84% conversion to 1,6-heptadiene in 79% yield in 15 h (TON 3950). In a run employing 10000 equivalents of cyclopentene and 99.995% ethylene the yield is 58% and TON 5800 in 20 h. It should be noted that the cost of 1,6-heptadiene in small quantities from a typical commercial source is approximately two orders of magnitude greater than the cost of cyclopentene plus ethylene.

EXAMPLE 2

The following example provides information regarding the methods and materials employed in Example 1.

General. All manipulations of air and moisture sensitive materials were conducted under a nitrogen atmosphere in a Vacuum Atmospheres drybox or on a dual-manifold Schlenk line. The glassware, including NMR tubes were oven-dried prior to use. Ether, pentane, toluene, dichloromethane, toluene and benzene were degassed with dinitrogen and passed through activated alumina columns and stored over 4 Å Linde-type molecular sieves. Dimethoxyethane, cyclooctene, and cyclopentene were vacuum distilled from a dark purple solution of sodium benzophenone ketyl, and degassed three times by freeze-pump-thaw technique. The deuterated solvents were dried over 4 Å Linde-type molecular sieves prior to use. $^1$H and $^{13}$C NMR spectra were acquired at room temperature unless otherwise noted using Varian spectrometers and referenced to the residual $^1$H/$^{13}$C resonances of the deuterated solvent ($^1$H: CDCl$_3$, δ 7.26; C$_6$D$_6$, δ 7.16; CD$_2$Cl$_2$, δ 5.32; C$_7$D$_8$, δ 7.09, 7.00, 6.98, 2.09. $^{13}$C: CDCl$_3$, δ 77.23; C$_6$D$_6$, δ 128.39; CD$_2$Cl$_2$, δ 54.00; C$_7$D$_8$, δ 137.86, 129.24, 128.33, 125.49, 20.4) and are reported as parts per million relative to tetramethylsilane. The elemental analysis was performed by Midwest Microlab, Indianapolis, Ind. The high pressure vessel equipped with a pressure gauge was purchased from Parr Instrument Company, Moline, Ill.

General Ethenolysis Procedure. Ethenolysis reactions were set up under an inert atmosphere in a glovebox: a Fisher-Porter bottle or a high pressure vessel equipped with a stir bar was charged with the appropriate amount of olefin (methyl oleate, cyclooctene, or cyclopentene) and with a mesitylene solution of the olefin metathesis catalyst of the desired concentration and volume. The mesitylene was used as internal standard. The head of the Fisher-Porter bottle equipped with a pressure gauge was adapted on the bottle. The system was sealed and taken out of the glovebox to an ethylene line. The vessel was then pressurized to the desired pressure. The reaction mixture was stirred at room temperature overnight. The reactions were then quenched with 10 uL (microliters) of 2-bromo-benzaldehyde and analyzed by gas chromatography (GC). Benzene was used as solvent for the ethenolysis reactions with 50 and 500 equiv of substrate. All the other runs were performed neat. For each entry, two identical reactions were performed and the data were averaged.

GC Analytical Method for Methyl Oleate. The GC analyses were run using a flame ionization detector (FID). Column: Rtx-1 from Restek; 30 m×0.25 mm (i d)×1.0 um (micrometer) film thickness. GC and column conditions: injector temperature 250° C.; detector temperature 250° C.; oven temperature, starting temperature 100° C., hold 5 min, ramp rate 10° C./min to 200° C., hold time 0 min; ramp rate 50° C./min to 300° C., hold time 8 min; carrier gas nitrogen.

GC Analytical Method for Cyclooctene and Cyclopentene. The GC analyses were run using a flame ionization detector (FID). Column: HP-5 (Crosslinked 5% PH ME Siloxane); 30 m×0.32 mm (i.d.)×0.25 um film thickness. GC and column conditions: injector temperature 350° C.; detector temperature 350° C.; oven temperature 50° C.; carrier gas nitrogen.

Materials. Mo(NAr)(CHCMe$_2$Ph)(Me$_2$Pyr)$_2$ (Singh, R.; Czekelius, C.; Schrock, R. R.; Müller, P.; Hoveyda, A. H. Organometallics, 2007, 26, 2528), Mo(NAr)(CHCMe$_2$Ph)[OCMe(CF$_3$)$_2$]$_2$ (Bazan, G. C.; Oskam, J H.; Cho, H. N.; Park, L. Y.; Schrock, R. R. J. Am. Chem. Soc., 1991, 113, 6899.), Mo(NAr)(CHCMe$_2$Ph)(Me$_2$Pyr)(TPP) (Lee, Y.-J.; Schrock, R. R.; Hoveyda, A. H. J. Am. Chem. Soc., 2009, online 07/06), (R)— and (S)—Mo(NAr)(CHCMe$_2$Ph)(Me$_2$Pyr)(OBitet) (1a) ((a) Malcolmson, S. J.; Meek, S. J.; Sattely, E. S.; Schrock, R. R.; Hoveyda, A. H. Nature, 2008, 456, 933; (b) Sattely, E. S.; Meek, S. J.; Malcolmson, S. J.; Schrock, R. R.; Hoveyda, A. H. J. Am. Chem. Soc., 2009, 131, 943), Mo(NAd)(CHCMe$_2$Ph)(Me$_2$Pyr)(OBitet) (1b) (Ibrahem, I.; Yu, M.; Schrock, R. R.; Hoveyda, A. H. J. Am. Chem. Soc., 2009, 131, 3844), Mo(NAd)(CHCMe$_2$Ph)(Me$_2$Pyr)(TPP) (Flook, M. M.; Jiang, A. J.; Schrock, R. R.; Müller, P.; Hoveyda, A. H. J. Am. Chem. Soc., 2009, 131, 7962), Mo(NAd)(CHCMe$_2$Ph)(pyr)(HIPTO) (2a) (Flook, M. M.; Jiang, A. J.; Schrock, R. R.; Müller, P.; Hoveyda, A. H. J. Am. Chem. Soc., 2009, 131, 7962), and W(NAr)(C$_3$H$_6$)(Me$_2$Pyr)(OBitet) (Jiang, A. J.; Simpson, J. H.; Müller, P.; Schrock, R. R. J. Am. Chem. Soc., 2009, 131, 7770) were prepared as described in the literature.

Preparation of Mo(NAr)(CHCMe$_2$Ph)(2,5-Me$_2$NC$_4$H$_2$)(OSiPh$_3$). A cold solution of Ph$_3$SiOH (149 mg, 0.54 mmol, 1 equiv) in 5 mL diethyl ether was added dropwise to a cold solution of Mo(NAr)(CHCMe$_2$Ph)(2,5-Me$_2$NC$_4$H$_2$)$_2$ (319 mg, 0.54 mmol, 1 equiv) in 5 mL diethylether. The reaction mixture was stirred at room temperature for 30 min The volatile materials were removed under vacuum. The orange solid generated was recrystallized from diethylether to obtain 259 mg of orange crystals (yield=62%). $^1$H NMR (500 MHz, CD$_2$Cl$_2$) δ 11.85 (s, 1H, syn Mo=CH, J$_{CH}$=120.4 Hz), 7.54-7.08 (m, 23H, Ar), 5.79 (s, 2H, NC$_4$H$_2$), 3.72 (sept, 2H, MeCHMe, J=7.0 Hz), 2.11 (s, 6 H), CH$_3$), 1.62 (s, 3H, CH$_3$), 1.52 (s, 3H, CH$_3$), 1.06 (app d, 6H, MeCHMe), 0.96 (br, 6H, MeCHMe); $^{13}$C NMR (125 MHz, CD$_2$Cl$_2$) δ 286.7, 153.4, 148.6, 147.5, 136.4, 135.7, 135.5, 130.6, 130.4, 128.6, 128.4, 126.5, 126.3, 123.5, 109.7, 108.9, 108.1, 54.9, 31.9, 30.6, 30.4, 29.1, 23.8 (br), 17.3 (br). Anal. Calc'd for C$_{46}$H$_{52}$MoN$_2$OSi: C, 71.48; H, 6.78; N, 3.62; Found: C, 71.44; H, 6.69; N, 3.75.

Preparation of (S)— and (R)—Mo(NAr)(CH$_2$)(Me$_2$Pyr)(OBitet). Ethylene (1 equiv) was added to a solution of (S)-1a (25.5 mg, 1 equiv) in C$_7$D$_8$ (40 mM). The $^1$H NMR was recorded after 5 minutes at 10° C. The two methylidenes are observed in the ratio of 2:1. $^1$H NMR (500 MHz, C$_7$D$_8$, 10° C.) selected peaks δ 67% dH$_{alpha}$=12.35 (d, 1H, Mo=CH, J$_{HH}$=4.5 Hz), 12.13 (d, 1H, Mo=CH, J$_{HH}$=4.5 Hz); 33% at 10° C., dH$_{alpha}$=12.94 (d, 1H, Mo=CH, J$_{HH}$=4.0 Hz), 12.24 (d, 1H, Mo=CH, J$_{HH}$=4.0 Hz); When $^{13}$C$_2$H$_4$ was used, the following $^{13}$C NMR was observed. $^{13}$C NMR (125 MHz, C$_7$D$_8$, 10° C.) selected peaks δ 276.3 (Mo=CH$_2$), 275.9 (Mo=CH$_2$).

Preparation of Mo(NAr)(CH$_2$CH$_2$CH$_2$)(Me$_2$Pyr)(OBitet). Ethylene (1 atm) was added to a pentane solution of Mo(NAr)(CHCMe$_3$)(Me$_2$Pyr)(OBitet) (25.5 mg, 40 mM) in a J. Young tube. The reaction mixture was allowed to cool down to −78° C. The volatile materials were removed under vacuum at −78° C. A 1:1 mixture of pentane:tetramethylsilane was vacuum transferred at −78° C. Ethylene (1 atm) was added to the J. Young tube at 20° C. The solution was stored at −30° C. Orange crystals of Mo(NAr)(CH$_2$CH$_2$CH$_2$)(Me$_2$Pyr)(OBitet) (10 mg) were isolated in 40% yield. $^1$H NMR (500 MHz, C$_7$D$_8$, −70° C.) selected peaks dH$_{alpha}$=6.16, 5.69, 5.24, 5.03; dH$_{beta}$=0.74,-0.16. $^{13}$C NMR (125 MHz, C$_7$D$_8$, −70° C.) selected peaks dC$_{alpha}$=102.2, 101.2; dC$_{beta}$=−1.1. Anal. Calc'd for C$_{47}$H$_{64}$Br$_2$MoN$_2$O$_2$Si: C, 58.03; H, 6.63; N, 2.88; Found: C, 57.64; H, 6.77; N, 2.85. X-Ray quality crystals were grown from a mixture of pentane and tetramethylsilane at −30° C. and under 1 atm of ethylene.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method, comprising:
providing a catalyst having the structure:

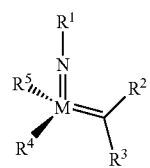

wherein M is Mo or W;
R$^1$ is aryl, heteroaryl, alkyl, heteroalkyl, optionally substituted;
R$^2$ and R$^3$ can be the same or different and are hydrogen, alkyl, alkenyl, heteroalkyl, heteroalkenyl, aryl, or heteroaryl, optionally substituted; and
R$^4$ and R$^5$ can be the same or different and are alkyl, heteroalkyl, aryl, heteroaryl, or silyl, optionally substituted, wherein at least one of $R^4$ or $R^5$ is a ligand containing oxygen bound to M; and reacting ethylene and a first species comprising at least one internal olefin in the presence of the catalyst to produce at least one product comprising a double bond, the double bond comprising a carbon atom from the ethylene and an atom of the first species, wherein the at least one product is formed at a turnover number of at least about 500; and wherein each optional substituent is independently selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl.

2. The method of claim 1, wherein one of $R^4$ and $R^5$ is a ligand containing oxygen bound to M, optionally substituted, and the other is a ligand containing nitrogen bound to M, optionally substituted, wherein each optional substituent is independently selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl.

3. The method of claim 1, wherein the at least one ligand containing oxygen bound to M lacks a plane of symmetry.

4. The method of claim 2, wherein the ligand containing nitrogen bound to M is selected from the group consisting of pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, and oxazinyl, all optionally substituted, wherein each optional substituent is independently selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl.

5. The method of claim 1, wherein the first species comprising at least one internal olefin is methyl oleate.

6. The method of claim 5, wherein the at least one product formed comprises 1-decene and methyl-9-decenoate.

7. The method of claim 2, wherein:
$R^1$ and $R^2$ are the same or different and are aryl or alkyl, optionally substituted;
$R^3$ is hydrogen; and
wherein each optional substituent is independently selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl.

8. The method of claim 2, wherein the ligand containing nitrogen bound to M has the structure:

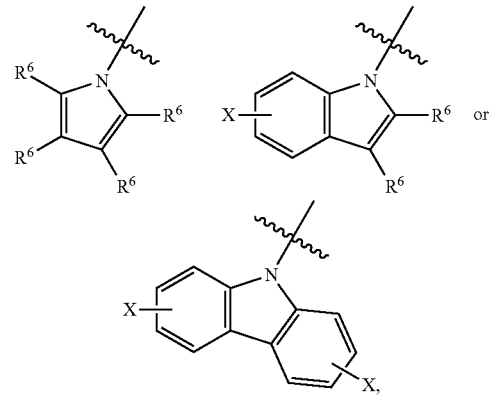

wherein each $R^6$ can be the same or different and is hydrogen, alkyl, heteroalkyl, aryl, or heteroaryl, optionally substituted; and each X may be present or absent and is independently a substituent, selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl.

9. The method of claim 1, wherein the ligand containing oxygen bound to M has the following structure:

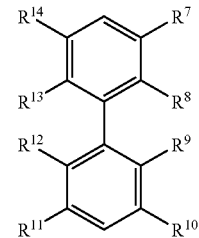

wherein $R^7$ is aryl, heteroaryl, alkyl, or heteroalkyl, optionally substituted;

$R^8$ is hydrogen, —OH, halogen, alkyl, heteroalkyl, aryl, heteroaryl, acyl, acyloxy, or —OP, optionally substituted; or, together $R^7$ and $R^8$ are joined to form a ring, optionally substituted;

$R^9$ is —OH, —OP, or amino, optionally substituted;

$R^{10}$ is hydrogen, halogen, alkyl, heteroalkyl, aryl, heteroaryl, or acyl, optionally substituted;

each $R^{11}$, $R^{12}$, $R^{13}$, and $R^{14}$ can be the same or different and is aryl, heteroaryl, alkyl, heteroalkyl, or acyl, optionally substituted; or, together $R^{11}$ and $R^{12}$ are joined to form a ring, optionally substituted; or together $R^{13}$ and $R^{14}$ are joined to form a ring, optionally substituted; and P is a hydroxyl protecting group; and wherein each optional substituent is independently selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl.

10. The method as in claim 1, wherein $R^4$ is silyl-protected BINOL derivative.

11. The method as in claim 1, wherein $R^1$ is:

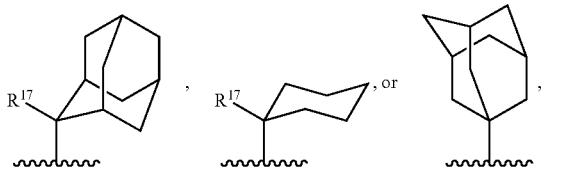

wherein each $R^{17}$ can be the same or different and is hydrogen, halogen, alkyl, heteroalkyl, aryl, acyl, or —OP, optionally substituted;

P is a hydroxyl protecting group; and wherein each optional substituent is independently selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl.

12. The method as in claim 1, wherein $R^1$ is

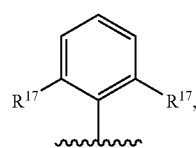

wherein each $R^{17}$ can be the same or different and is hydrogen, halogen, alkyl, heteroalkyl, aryl, acyl, or —OP, optionally substituted;

P is a hydroxyl protecting group; and wherein each optional substituent is independently selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl.

13. The method as in claim 1, wherein $R^2$ is alkyl.

14. The method as in claim 1, wherein $R^1$ is

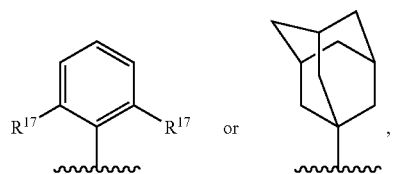

wherein each $R^{17}$ can be the same or different and is hydrogen, halogen, alkyl, heteroalkyl, aryl, acyl, or —OP, optionally substituted;

$R^2$ is $CMe_2Ph$ or $CMe_3$;

$R^3$ is H; and $R^4$ is an enantiomer of the following structure,

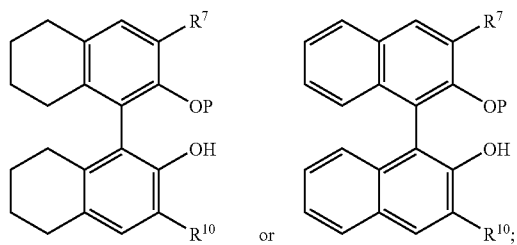

wherein each $R^7$ and $R^{10}$ is the same or different and is halogen, methyl, t-butyl, $CF_3$, or aryl, optionally substituted; and P is a hydroxyl protecting group; and wherein each optional substituent is independently selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl.

15. The method as in claim 14, wherein $R^5$ has the following structure:

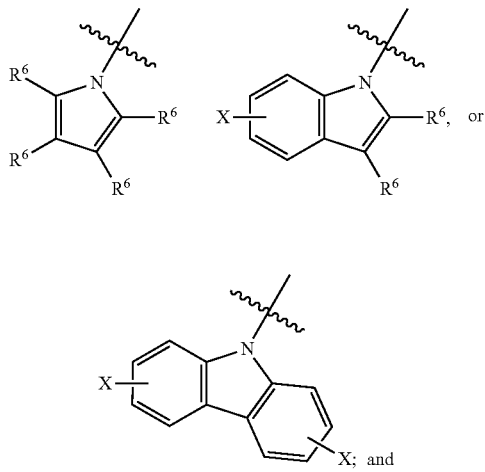

wherein each $R^6$ can be the same or different and is hydrogen, alkyl, heteroalkyl, aryl, heteroaryl, optionally substituted; and each X may be present or absent and is independently a substituent selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl.

16. The method of claim 1, wherein the ligand containing oxygen bound to M has the following structure:

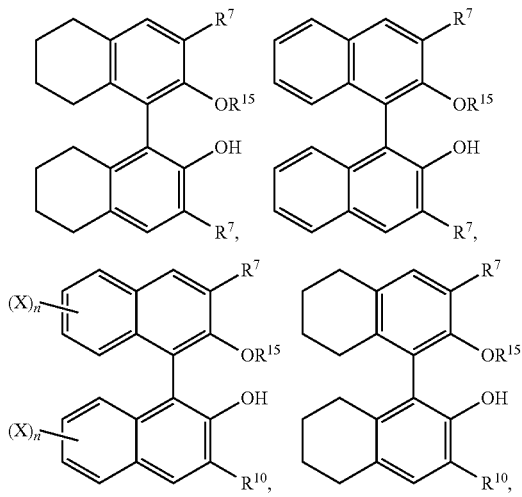

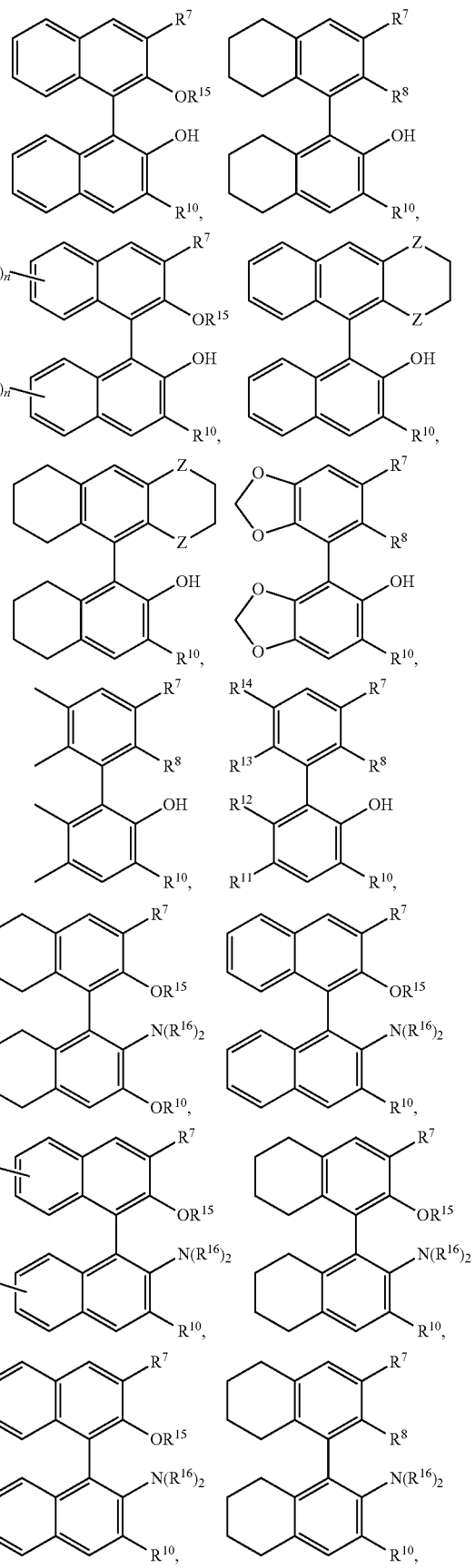

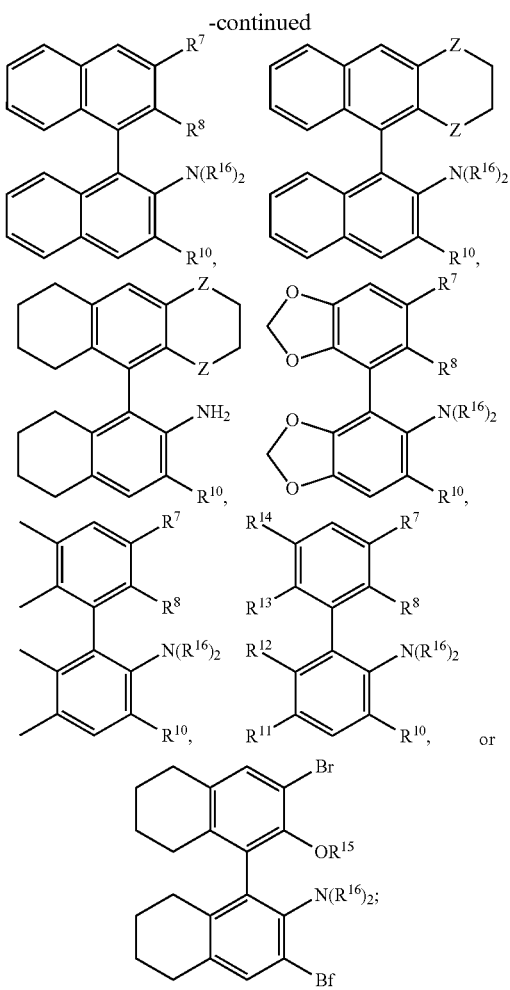

wherein each $R^7$ and $R^8$ can be the same or different and is hydrogen, halogen, alkyl, alkoxy, aryl, acyl, or a protecting group, optionally substituted;

$R^{10}$ is hydrogen, halogen, alkyl, heteroalkyl, aryl, heteroaryl, or acyl, optionally substituted;

each $R^{11}$, $R^{12}$, $R^{13}$, and $R^{14}$ can be the same or different and is aryl, heteroaryl, alkyl, heteroalkyl, or acyl, optionally substituted; or, together $R^{11}$ and $R^{12}$ are joined to form a ring, optionally substituted; or, together $R^{13}$ and $R^{14}$ are joined to form a ring, optionally substituted;

$R^{15}$ is alkyl, aryl, or a hydroxyl protecting group, optionally substituted;

$R^{16}$ is hydrogen or an amine protecting group;

each X may be present or absent and is independently a substituent-selected from alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, and arylalkyloxyalkyl, each Z can be the same or different and is $(CH_2)_m$, N, O, optionally substituted;

n is 0-5; and m is 1-4.

17. The method of claim 16, wherein $R^7$ and $R^{10}$ are the same or different and is selected from the group consisting of F, Cl, Br, or I.

18. The method of claim 1, wherein $R^2$ is $CMe_2Ph$ or $CMe_3$ and $R^3$ is hydrogen.

19. The method of claim 1, wherein M is Mo.

20. The method of claim 1, wherein the atom of the first species is carbon.

21. The method of claim 1, wherein the turnover number is at least about 1,000.

22. The method of claim 1, wherein the turnover number is at least about 5,000.

23. The method of claim 1, wherein the turnover number is at least about 10,000.

24. The method of claim 1, wherein the at least one product is formed at a selectivity of at least about 80%.

25. The method of claim 1, wherein the at least one product is formed at a selectivity of at least about 90%.

26. The method of claim 1, wherein the at least one product is formed at a selectivity of at least about 95%.

27. The method of claim 1, wherein the at least one product is formed at a conversion of at least about 60%.

28. The method of claim 1, wherein the at least one product is formed at a conversion of at least about 70%.

29. The method of claim 1, wherein the at least one product is formed at a conversion of at least about 80%.

30. The method of claim 1, wherein the at least one product is formed at a conversion of at least about 90%.

31. The method of claim 1, wherein the first species comprising at least one internal olefin is cyclic.

32. The method of claim 1, wherein the first species comprising at least one internal olefin is non-cyclic.

33. The method of claim 1, wherein the first species comprising at least one internal olefin is symmetric.

34. The method of claim 1, wherein the first species comprising at least one internal olefin is non-symmetric.

35. The method of claim 1, wherein the first species comprising at least one internal olefin comprises at least one heteroatom.

36. The method of claim 1, wherein the first species comprising at least one internal olefin comprises at least two double bonds.

* * * * *

UNITED STATES PATENT AND TRADEMARK OFFICE
CERTIFICATE OF CORRECTION

PATENT NO. : 8,222,469 B2
APPLICATION NO. : 12/503608
DATED : July 17, 2012
INVENTOR(S) : Richard R. Schrock et al.

Page 1 of 1

It is certified that error appears in the above-identified patent and that said Letters Patent is hereby corrected as shown below:

Please delete the paragraph titled 'STATEMENT REGARDING FEDERALLY SPONSORED RESEARCH OR DEVELOPMENT' encompassing column 1, lines 8-11:

"This invention was made with the support under the following government contract CHE-0554734 awarded by the National Science Foundation. The government has certain rights in the invention."

and replace with:

--This invention was made with government support under Grant No. CHE0554734 awarded by the National Science Foundation. The government has certain rights in this invention.--

Signed and Sealed this
Twentieth Day of November, 2012

David J. Kappos
*Director of the United States Patent and Trademark Office*